United States Patent
Bennett et al.

(10) Patent No.: US 11,414,488 B2
(45) Date of Patent: Aug. 16, 2022

(54) METHODS FOR TREATING CANCER

(71) Applicant: BicycleRD Limited, Cambridge (GB)

(72) Inventors: Gavin Bennett, Cambridge (GB); Gillian Langford, Cambridge (GB); Peter Park, Lexington, MA (US); Johanna Lahdenranta, Lexington, MA (US)

(73) Assignee: BICYCLERD LIMITED, Cambridge (GB)

( * ) Notice: Subject to any disclaimer, the term of this patent is extended or adjusted under 35 U.S.C. 154(b) by 0 days.

(21) Appl. No.: 16/871,305

(22) Filed: May 11, 2020

(65) Prior Publication Data

US 2020/0354456 A1    Nov. 12, 2020

Related U.S. Application Data

(60) Provisional application No. 62/846,064, filed on May 10, 2019.

(51) Int. Cl.
| C07K 16/28 | (2006.01) |
| A61P 35/00 | (2006.01) |
| A61K 9/00 | (2006.01) |
| A61K 38/12 | (2006.01) |
| A61K 47/18 | (2017.01) |
| A61K 47/26 | (2006.01) |
| A61K 39/00 | (2006.01) |

(52) U.S. Cl.
CPC ........ *C07K 16/2818* (2013.01); *A61K 9/0019* (2013.01); *A61K 38/12* (2013.01); *A61K 47/183* (2013.01); *A61K 47/26* (2013.01); *A61P 35/00* (2018.01); *A61K 2039/505* (2013.01)

(58) Field of Classification Search
None
See application file for complete search history.

(56) References Cited

U.S. PATENT DOCUMENTS

| 10,441,663 | B2 | 10/2019 | Bennett et al. |
| 10,532,106 | B2 | 1/2020 | Teufel et al. |
| 10,624,968 | B2 | 4/2020 | Bennett et al. |
| 10,792,368 | B1 | 10/2020 | Teufel et al. |
| 10,857,196 | B2 | 12/2020 | Beswick et al. |
| 10,899,798 | B2 | 1/2021 | Bennett et al. |
| 10,919,937 | B2 | 2/2021 | Beswick et al. |
| 10,994,019 | B2 | 5/2021 | Teufel et al. |
| 2018/0169254 | A1 | 6/2018 | Bennett et al. |
| 2018/0311300 | A1 | 11/2018 | Beswick et al. |
| 2019/0134213 | A1 | 5/2019 | Teufel et al. |
| 2019/0389907 | A1 | 12/2019 | Teufel et al. |
| 2020/0129630 | A1 | 4/2020 | Koehler et al. |
| 2020/0131228 | A1 | 4/2020 | Beswick et al. |
| 2020/0171161 | A1 | 6/2020 | Teufel et al. |
| 2020/0215199 | A1 | 7/2020 | Bennett et al. |
| 2020/0316209 | A1 | 10/2020 | Teufel et al. |
| 2020/0407709 | A1 | 12/2020 | Chen et al. |
| 2021/0046145 | A1 | 2/2021 | Beswick et al. |
| 2021/0079045 | A1 | 3/2021 | Bennett et al. |
| 2021/0147484 | A1 | 5/2021 | Beswick et al. |

FOREIGN PATENT DOCUMENTS

| WO | WO-2016/067035 A1 | 5/2016 |
| WO | WO-16067035 A1 | 6/2016 |
| WO | WO-17191460 A1 | 11/2017 |
| WO | WO-18096365 A1 | 5/2018 |
| WO | WO-2018/115203 A1 | 6/2018 |
| WO | WO-2018/127699 A1 | 7/2018 |
| WO | WO-2018/197509 A1 | 11/2018 |
| WO | WO-18197893 A1 | 11/2018 |
| WO | WO-2019/002842 A1 | 1/2019 |
| WO | WO-20084305 A1 | 4/2020 |
| WO | WO-20089627 A1 | 5/2020 |
| WO | WO-2020/178574 A1 | 9/2020 |
| WO | WO-2021/074647 A1 | 4/2021 |

OTHER PUBLICATIONS

Hu-Lieskovan et al. ("New combination strategies using PD-1/L! checkpoint inhibitors as a backbone" Cancer J. 2017; 23(1):10-22).*
Baek et al. ("Effects of Histidine and Sucrose on the Biophysical Properties of a Monoclonal Antibody" Pharm Res (2017) 34:629-639).*
National Cancer Institute (<https://www.cancer.gov/about-cancer/understanding/what-is-cancer> accessed Apr. 9, 2021).*
Merck Manual (https://www.merckmanuals.com/home/digestive-disorders/tumors-of-the-digestive-system/pancreatic-cancer?query=pancreatic%20cancer accessed Apr. 9, 2021).*
Merck Manual (https://www.merckmanuals.com/home/blood-disorders/plasma-cell-disorders/multiple-myeloma?query=multiple%20myeloma accessed Apr. 9, 2021).*
U.S. Appl. No. 16/838,367, filed Apr. 2, 2020.
Moraes et al., "Immune Checkpoint Inhibitors (anti PD-1 or anti PD-L1) versus chemotherapy for Second or Thrd-Line Treatment of Metastic Non-Small Cell Lung Cancer (Protocol)," Cochrane Database of Systematic Reviews, vol. 4, 2017.
Reagan-Shaw et al., "Dose Translation from Animal to Human Studies Revisted," The FASEB Journal, Life Sciences Forum, 22:3, 2008.
PCT International Search Report and Written Opinion for PCT/GB2020/051140, dated Aug. 20, 2020.

* cited by examiner

*Primary Examiner* — Julie Ha
*Assistant Examiner* — Tara L Martinez
(74) *Attorney, Agent, or Firm* — Dechert LLP; Andrea L. C. Reid; Gang Wang

(57) ABSTRACT

The present invention relates to a method of treating a cancer in a patient.

21 Claims, 8 Drawing Sheets

METHODS FOR TREATING CANCER

CROSS-REFERENCE TO RELATED APPLICATIONS

This application claims the benefit under 35 U.S.C. § 119(e) of U.S. Provisional Application No. 62/846,064, filed May 10, 2019, the content of which is incorporated by reference herein in its entirety.

TECHNICAL FIELD OF THE INVENTION

The present invention relates to use of a Bicycle toxin conjugate BT1718, or a pharmaceutically acceptable salt thereof, in combination with a checkpoint inhibitor, for treating cancer. The present invention also provides pharmaceutically acceptable compositions comprising BT1718, or a pharmaceutically acceptable salt thereof, and a checkpoint inhibitor.

BACKGROUND OF THE INVENTION

MT1-MMP is a transmembrane metalloprotease that plays a major role in the extracellular matrix remodelling, directly by degrading several of its components and indirectly by activating pro-MMP2. MT1-MMP is crucial for tumor angiogenesis (Sounni et al (2002) FASEB J. 16(6), 555-564) and is over-expressed on a variety of solid tumors. Accordingly, there remains a high unmet need in developing inhibitors of MT1-MMP for the treatment of cancer.

SUMMARY OF THE INVENTION

It has now been found that a combination of BT1718, or a pharmaceutically acceptable salt thereof, and a checkpoint inhibitor vastly improves anti-tumor activity compared to each of the single agent treatment. Accordingly, in one aspect, the present invention provides a composition comprising BT1718, or a pharmaceutically acceptable salt thereof, and a checkpoint inhibitor.

In another aspect, the present invention provides a method for treating a cancer in a patient, comprising administering to the patient a therapeutically effective amount of BT1718, or a pharmaceutically acceptable salt thereof, and a checkpoint inhibitor.

DETAILED DESCRIPTION OF CERTAIN EMBODIMENTS

Figure 1:
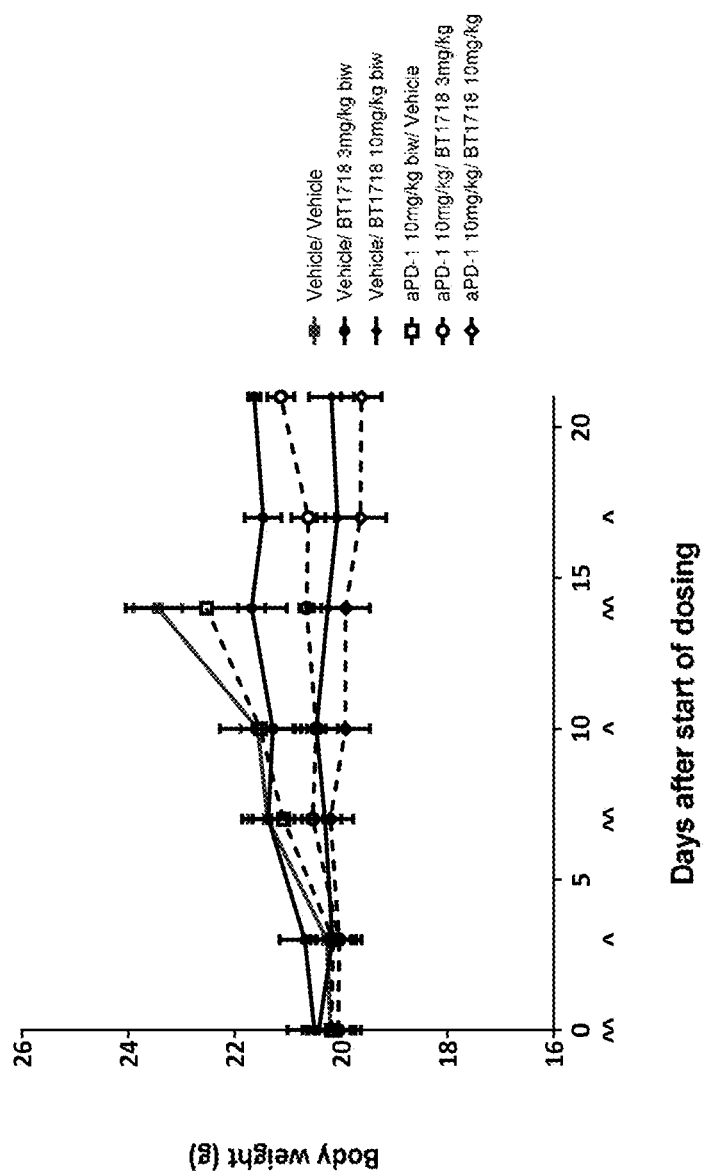
FIG. 1 depicts body weight changes after the treatment of BT1718 and PD-1 to C57BL/6 mice bearing 3LL tumor. Data points represent group mean body weight. Error bars represent standard error of the mean (SEM).

1. Description of Certain Embodiments of the Invention

It has been found that a combination of BT1718, or a pharmaceutically acceptable salt thereof, and a checkpoint inhibitor exhibited a surprising and great improvement on anti-tumor activity compared to each of the single agent treatment. For example, a BT1718 and anti-PD-1 antibody combination vastly improves survival rate in lung carcinoma model compared to each of the single agent treatments (see, for example, Example 2). In addition, a BT1718 and anti-PD-1 antibody combination exhibited increased anti-tumor activity compared to monotherapies in breast cancer Adenocarcinoma model (see, for example, Example 3). Further, a BT1718 and anti-CTLA-4 antibody combination exhibited potent anti-tumour activity: complete regressions, enhanced survival and immunologic memory in colon carcinoma model (see, for example, Example 4).

Accordingly, in one aspect, the present invention provides a method for treating a cancer in a patient, comprising administering to the patient a therapeutically effective amount of BT1718, or a pharmaceutically acceptable salt thereof, and a checkpoint inhibitor.

In some embodiments, the present invention provides a use of BT1718 or a pharmaceutically acceptable salt thereof in the manufacture of a medicament for treating cancer, wherein the medicament is used in combination with a checkpoint inhibitor.

In some embodiments, BT1718, or a pharmaceutically acceptable salt thereof, is administered at a dose of about 3-46 mg/m$^2$. In some embodiments, BT1718, or a pharmaceutically acceptable salt thereof, is administered at a dose of about 3-13 mg/m$^2$, about 14-24 mg/m$^2$, about 25-35 mg/m$^2$, or about 36-46 mg/m$^2$. In some embodiments, BT1718, or a pharmaceutically acceptable salt thereof, is administered at a dose of about 9-36 mg/m$^2$, about 9-30 mg/m$^2$, about 9-24 mg/m$^2$, or about 9-18 mg/m$^2$. In some embodiments, BT1718, or a pharmaceutically acceptable salt thereof, is administered at a dose of about 9 mg/m$^2$. In some embodiments, BT1718, or a pharmaceutically acceptable salt thereof, is administered at a dose of about 14.4 mg/m$^2$. In some embodiments, BT1718, or a pharmaceutically acceptable salt thereof, is administered at a dose of about 18.6 mg/m$^2$. In some embodiments, BT1718, or a pharmaceutically acceptable salt thereof, is administered at a dose of about 19.2 mg/m$^2$.

In some embodiments, BT1718, or a pharmaceutically acceptable salt thereof, is administered at a frequency of 1-4 times a week. In some embodiments, BT1718, or a pharmaceutically acceptable salt thereof, is administered at a frequency of once a week. In some embodiments, BT1718, or a pharmaceutically acceptable salt thereof, is administered at a frequency of 2, 3, or 4 times a week. In some embodiments, BT1718, or a pharmaceutically acceptable salt thereof, is administered at a frequency of once every 1.5 weeks. In some embodiments, BT1718, or a pharmaceutically acceptable salt thereof, is administered at a frequency of once every 2 weeks. In some embodiments, BT1718, or a pharmaceutically acceptable salt thereof, is administered at a frequency of once every 2.5 weeks. In some embodiments, BT1718, or a pharmaceutically acceptable salt thereof, is administered at a frequency of once every 3 weeks. In some embodiments, BT1718, or a pharmaceutically acceptable salt thereof, is administered at a frequency of once every 4 weeks.

In some embodiments, BT1718, or a pharmaceutically acceptable salt thereof, is administered for a treatment period of about 1-4 weeks. In some embodiments, BT1718, or a pharmaceutically acceptable salt thereof, is administered for a treatment period of about 5-8 weeks. In some embodiments, BT1718, or a pharmaceutically acceptable salt thereof, is administered for a treatment period of about 9-12 weeks. In some embodiments, BT1718, or a pharmaceutically acceptable salt thereof, is administered for a treatment period of about 13-20 weeks. In some embodiments, BT1718, or a pharmaceutically acceptable salt thereof, is administered for a treatment period of about 21-28 weeks. In some embodiments, BT1718, or a pharmaceutically acceptable salt thereof, is administered for a treatment period of about 4, 8, 12, 16, 20, 24, or 28 weeks. In some embodiments, BT1718, or a pharmaceutically acceptable salt thereof, is administered for a treatment period of about 30 weeks, or longer.

In some embodiments, BT1718, or a pharmaceutically acceptable salt thereof, is administered to a patient by an intravenous bolus injection. In some embodiments, BT1718, or a pharmaceutically acceptable salt thereof, is administered to a patient by an intravenous infusion. In some embodiments, an intravenous infusion of BT1718, or a pharmaceutically acceptable salt thereof, is an about 5-10 minute infusion. In some embodiments, an intravenous infusion of BT1718, or a pharmaceutically acceptable salt thereof, is an about 10-20 minute infusion. In some embodiments, an intravenous infusion of BT1718, or a pharmaceutically acceptable salt thereof, is an about 20-40 minute infusion. In some embodiments, an intravenous infusion of BT1718, or a pharmaceutically acceptable salt thereof, is an about 45, or 50, or 55 minute infusion. In some embodiments, an intravenous infusion of BT1718, or a pharmaceutically acceptable salt thereof, is an about 1 hour infusion. In some embodiments, an intravenous infusion of BT1718, or a pharmaceutically acceptable salt thereof, is an about 1-1.5 hr infusion. In some embodiments, an intravenous infusion of BT1718, or a pharmaceutically acceptable salt thereof, is an about 1.5-2 hr infusion. In some embodiments, an intravenous infusion of BT1718, or a pharmaceutically acceptable salt thereof, is an about 2-3 hr infusion. In some embodiments, an intravenous infusion of BT1718, or a pharmaceutically acceptable salt thereof, is a more than 3 hr infusion.

A checkpoint inhibitor is administered at the dosage regimen according to FDA recommendation or approval. In some embodiments, a checkpoint inhibitor is administered at a dose of about 1-20 mg/kg. In some embodiments, a checkpoint inhibitor is administered at a dose of about 1-5 mg/kg, about 6-10 mg/kg, about 11-15 mg/kg, or about 16-20 mg/kg. In some embodiments, a checkpoint inhibitor is administered at a dose of about 1-10 mg/kg, about 5-15 mg/kg, or about 10-20 mg/kg. In some embodiments, a checkpoint inhibitor is administered at a dose of about 2, 3, 4, 5, 6, 7, 8, 9, or 10 mg/kg. In some embodiments, a checkpoint inhibitor is administered at a dose of about 11, 12, 13, 14, 15, 16, 17, 18, 19, or 20 mg/kg. In some embodiments, a checkpoint inhibitor is administered at a frequency of 1-4 times a week. In some embodiments, a checkpoint inhibitor is administered at a frequency of once a week. In some embodiments, a checkpoint inhibitor is administered at a frequency of 2, 3, or 4 times a week. In some embodiments, a checkpoint inhibitor is administered at a frequency of once every 1.5 weeks. In some embodiments, a checkpoint inhibitor is administered at a frequency of once every 2 weeks. In some embodiments, a checkpoint inhibitor is administered at a frequency of once every 2.5 weeks. In some embodiments, a checkpoint inhibitor is administered at a frequency of once every 3 weeks. In some embodiments, a checkpoint inhibitor is administered at a frequency of once every 4 weeks. In some embodiments, a checkpoint inhibitor is administered for a treatment period of about 1-4 weeks. In some embodiments, a checkpoint inhibitor is administered for a treatment period of about 9-12 weeks, about 13-20 weeks, about 21-28 weeks, or about 29-36 weeks. In some embodiments, a checkpoint inhibitor is administered for a treatment period of about 36 weeks, or longer. In some embodiments, a checkpoint inhibitor is administered to a patient by an intravenous injection. In some embodiments, a checkpoint inhibitor is administered to a patient by an intravenous infusion. In some embodiments, an intravenous infusion of a checkpoint inhibitor is an about 5-10 minute infusion. In some embodiments, an intravenous infusion of a checkpoint inhibitor is an about 10-20 minute or about 20-40 minute infusion. In some embodiments, an intravenous infusion of a checkpoint inhibitor is an about 30, 40, 45, 50, 55, or 60 minute infusion. In some embodiments, an intravenous infusion of a checkpoint inhibitor is an about 1-1.5 hr, about 1.5-2 hr, or about 2-3 hr infusion.

In some embodiments, a medicament comprising BT1718, or a pharmaceutically acceptable salt thereof, is selected from the BT17118 formulations as shown in the instant examples. In some embodiments, a medicament comprising BT1718, or a pharmaceutically acceptable salt thereof, further comprises histidine. In some embodiments, a medicament comprising BT1718, or a pharmaceutically acceptable salt thereof, and histidine is at about pH 7. In some embodiments, a medicament comprising BT1718, or a pharmaceutically acceptable salt thereof, further comprises sucrose. In some embodiments, a medicament comprising BT1718, or a pharmaceutically acceptable salt thereof, further comprises about 10% w/v sucrose. In some embodiments, a medicament comprising BT1718, or a pharmaceutically acceptable salt thereof, further comprises water. In some embodiments, the present invention provides a medicament comprising BT1718, or a pharmaceutically acceptable salt thereof, histidine, sucrose, and water, wherein the medicament is at about pH 7. In some embodiments, the present invention provides a medicament comprising BT1718, or a pharmaceutically acceptable salt thereof, histidine, sucrose, and water, wherein the medicament is at about pH 6.6. In some embodiments, a medicament comprises BT1718, or a pharmaceutically acceptable salt thereof, at a concentration of about 0.48 mg/ml. In some embodiments, a medicament comprises BT1718, or a pharmaceutically acceptable salt thereof, at a concentration of about 0.62 mg/ml. In some embodiments, a medicament comprises BT1718, or a pharmaceutically acceptable salt thereof, at a concentration of about 0.96 mg/ml.

In some embodiments, a checkpoint inhibitor is selected from those as described herein.

In some embodiments, a cancer is selected from those as described herein.

2. Compounds and Definitions

BT1718 (or BT17BDC-18) has the structure shown below. Preparation of BT1718 is described in detail in WO 2016/067035, filed Oct. 29, 2015, the entirety of which is hereby incorporated herein by reference.

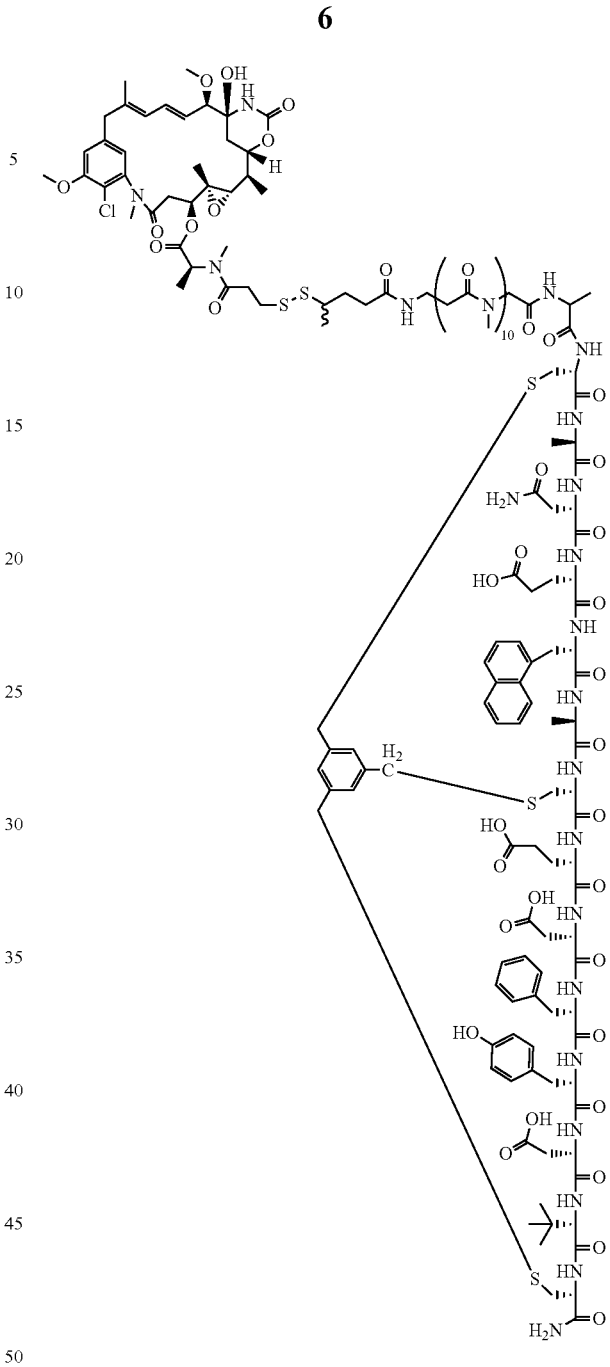

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

As used herein, the term "about" refers to within 20% of a given value. In some embodiments, the term "about" refers to within 20%, 19%, 18%, 17%, 16%, 15%, 14%, 13%, 12%, 11%, 10%, 9%, 8%, 7%, 6%, 5%, 4%, 3%, 2%, or 1% of a given value.

As used herein, the term "mg/kg" refers to the milligram of medication per kilogram of the body weight of the subject taking the medication. As provided by the FDA guidance, a dose in mg/kg in an animal can be converted to a corresponding Human Equivalent Dose (HED) in $mg/m^2$. For example, a conversion between doses in mouse and HED is shown below:

| Mouse Dose (mg/kg) | Human Equivalent Dose $(mg/m^2)$ |
|---|---|
| 2.4 | 7.2 |
| 3.0 | 9.0 |
| 4.8 | 14.4 |
| 6.4 | 19.2 |
| 10.0 | 30.0 |

3. Pharmaceutically Acceptable Compositions

According to some embodiments, the present invention provides a pharmaceutical composition comprising BT1718, or a pharmaceutically acceptable salt thereof, and a checkpoint inhibitor. In some embodiments, the present invention provides a pharmaceutical composition for use in treatment of a cancer, comprising BT1718, or a pharmaceutically acceptable salt thereof, and a checkpoint inhibitor.

In some embodiments, a composition comprises a pharmaceutically acceptable carrier, adjuvant, or vehicle. The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "patient," as used herein, means an animal, preferably a mammal, and most preferably a human.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Pharmaceutically acceptable compositions of this invention may also be formulated for oral administration. Such formulations may be administered with or without food. In some embodiments, pharmaceutically acceptable compositions of this invention are administered without food. In other embodiments, pharmaceutically acceptable compositions of this invention are administered with food.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

4. Methods for Treating Cancers

According to some embodiments, the present invention provides a method of treating a cancer in a patient, comprising administering to the patient a therapeutically effective amount of BT1718, or a pharmaceutically acceptable salt thereof, and a checkpoint inhibitor.

In some embodiments, the present invention provides a use of BT1718, or a pharmaceutically acceptable salt thereof, in combination with a checkpoint inhibitor, for treatment of a cancer.

In some embodiments, a cancer is a lung cancer. In some embodiments, a lung cancer is a met-amplified squamous NSCLC, a squamous cell NSCLC with wild type EGFR, or a T790M EGFR-expressing lung adenocarcinoma.

In some embodiments, the present invention provides a method of treating a lung cancer in a patient, comprising administering to the patient BT1718, or a pharmaceutically acceptable salt thereof, and an anti-PD1 antibody. In some embodiments, BT1718, or a pharmaceutically acceptable salt thereof, is administered at a dose of 9 mg/m$^2$ at a frequency of 2 times a week. In some embodiments, BT1718, or a pharmaceutically acceptable salt thereof, is administered at a dose of 30 mg/m$^2$ at a frequency of 2 times a week. In some embodiments, BT1718, or a pharmaceutically acceptable salt thereof, is administered at a dose of 14.4 mg/m$^2$ at a frequency of once a week. In some embodiments, an anti-PD1 antibody is administered at a dose and frequency as described herein. In some embodiments, BT1718, or a pharmaceutically acceptable salt thereof, and/or an anti-PD1 antibody is administered by iv injection, or iv infusion as described herein.

In some embodiments, a cancer is a breast cancer. In some embodiments, a breast cancer is a triple negative breast cancer. In some embodiments, a breast cancer is a basaloid triple negative breast cancer.

In some embodiments, the present invention provides a method of treating a breast cancer in a patient, comprising administering to the patient BT1718, or a pharmaceutically acceptable salt thereof, and an anti-PD1 antibody. In some embodiments, BT1718, or a pharmaceutically acceptable salt thereof, is administered at a dose of 14.4 mg/m$^2$ at a frequency of once a week. In some embodiments, BT1718, or a pharmaceutically acceptable salt thereof, is administered at a dose of 18.6 mg/m² at a frequency of once a week. In some embodiments, an anti-PD1 antibody is administered at a dose and frequency as described herein. In some embodiments, BT1718, or a pharmaceutically acceptable salt thereof, and/or an anti-PD1 antibody is administered by iv injection, or iv infusion as described herein.

In some embodiments, a cancer is a colon cancer. In some embodiments, a cancer is a colorectal adenocarcinoma. In some embodiments, a colorectal adenocarcinoma is a high pgp-expressing colorectal adenocarcinoma.

In some embodiments, the present invention provides a method of treating a colon cancer in a patient, comprising administering to the patient BT1718, or a pharmaceutically acceptable salt thereof, and an anti-CTLA4 antibody. In some embodiments, BT1718, or a pharmaceutically acceptable salt thereof, is administered at a dose of 19.2 mg/m² at a frequency of once a week. In some embodiments, an anti-CTLA4 antibody is administered at a dose and frequency as described herein. In some embodiments, BT1718, or a pharmaceutically acceptable salt thereof, and/or an anti-CTLA4 antibody is administered by iv injection, or iv infusion as described herein.

In some embodiments, a cancer is a gastric cancer. In some embodiments, a gastric cancer is a FGFR-amplified gastric cancer.

In some embodiments, a cancer is a head and neck cancer. In some embodiments, a head and neck cancer is a nasal septum squamous cell carcinoma.

In some embodiments, a cancer is a sarcoma. In some embodiments, a sarcoma is a fibrosarcoma. In some embodiments, a fibrosarcoma is an N-ras mutant/IDH1 mutant soft tissue sarcoma (STS).

In some embodiments, a cancer is a bladder cancer. In some embodiments, a bladder cancer is selected from the group consisting of basal, p53-like, and luminal.

In some embodiments, a cancer is an endometrial cancer. In some embodiments, an endometrial cancer is selected from the group consisting of MMR-D, POLE EDM, p53 WT, p53 abnormal, Type I, Type II, carcinoma, carcinosarcoma, endometrioid adenocarcinoma, serous carcinoma, clear cell carcinoma, mucinous carcinoma, mixed or undifferentiated carcinoma, mixed serous and endometrioid, mixed serous and low-grade endometrioid, and undifferentiated.

In some embodiments, a cancer is an esophageal cancer. In some embodiments, an esophageal cancer is selected from the group consisting of adenocarcinoma (EAC), squamous cell carcinoma (ESCC), chromosomal instability (CIN), Epstein-Barr virus (EBV), genomically stable (GS), and microsatellite instability (MSI).

In some embodiments, a cancer is a glioblastoma. In some embodiments, a glioblastoma is selected from the group consisting of proneural, neural, classical, and mesenchymal.

In some embodiments, a cancer is a mesothelioma. In some embodiments, a mesothelioma is selected from the group consisting of pleural, peritoneal, pericardial, epithelioid, sarcomatoid, biphasic, and malignant.

In some embodiments, a cancer is a multiple myeloma. In some embodiments, a multiple myeloma is selected from the group consisting of hyperdiploid, non-hyperdiploid, cyclin D translocation, MMSET translocation, MAF translocation, and unclassified.

In some embodiments, a cancer is an ovarian cancer. In some embodiments, an ovarian cancer is selected from the group consisting of clear cell, endometrioid, mucinous, high-grade serous and low-grade serous.

In some embodiments, a cancer is a pancreatic cancer. In some embodiments, a pancreatic cancer is selected from the group consisting of squamous, pancreatic progenitor, immunogenic, and ADEX (Aberrantly Differentiated Endocrine eXocrine).

In some embodiments, a cancer is a prostate cancer. In some embodiments, a prostate cancer is selected from the group consisting of AZGP1 (subtype I), MUC1 (subtype II), and MUC1 (subtype III).

In some embodiments, a checkpoint inhibitor is an anti-PD1 antibody. In some embodiments, an anti-PD1 antibody is selected from nivolumab (anti-PD-1 antibody, Opdivo®, Bristol-Myers Squibb); pembrolizumab (anti-PD-1 antibody, Keytruda®, Merck); durvalumab (anti-PD-L1 antibody, Imfinzi®, AstraZeneca); and atezolizumab (anti-PD-L1 antibody, Tecentriq®, Genentech).

In some embodiments, a checkpoint inhibitor is an anti-CTLA-4 antibody. In some embodiments, an anti-CTLA-4 antibody is ipilimumab (anti-CTLA-4 antibody, Yervoy®, Bristol-Myers Squibb).

In some embodiments, the present invention provides a method of treating a cancer in a patient, comprising administering to the patient BT1718, or a pharmaceutically acceptable salt thereof, at a dose level of about 3 mg/kg, and a checkpoint inhibitor at a dose level of about 10 mg/kg. In some embodiments, each of BT1718, or a pharmaceutically acceptable salt thereof, and a checkpoint inhibitor is administered at a frequency of twice a week. In some embodiments, each of BT1718, or a pharmaceutically acceptable salt thereof, and a checkpoint inhibitor is administered at a frequency of once every 3 days.

In some embodiments, the present invention provides a method of treating a cancer in a patient, comprising administering to the patient BT1718, or a pharmaceutically acceptable salt thereof, at a dose level of about 10 mg/kg, and a checkpoint inhibitor at a dose level of about 10 mg/kg. In some embodiments, each of BT1718, or a pharmaceutically acceptable salt thereof, and a checkpoint inhibitor is administered at a frequency of twice a week. In some embodiments, each of BT1718, or a pharmaceutically acceptable salt thereof, and a checkpoint inhibitor is administered at a frequency of once every 3 days.

In some embodiments, the present invention provides a method of treating a cancer in a patient, comprising administering to the patient BT1718, or a pharmaceutically acceptable salt thereof, at a dose level of about 4.8 mg/kg, and a checkpoint inhibitor at a dose level of about 10 mg/kg. In some embodiments, BT1718, or a pharmaceutically acceptable salt thereof, is administered at a frequency of once a week, and a checkpoint inhibitor is administered at a frequency of twice a week. In some embodiments, BT1718, or a pharmaceutically acceptable salt thereof, is administered at a frequency of once a week, and a checkpoint inhibitor is administered at a frequency of once every 3 days.

In some embodiments, the present invention provides a method of treating a cancer in a patient, comprising administering to the patient BT1718, or a pharmaceutically acceptable salt thereof, at a dose level of about 6.2 mg/kg, and a checkpoint inhibitor at a dose level of about 10 mg/kg. In some embodiments, BT1718, or a pharmaceutically acceptable salt thereof, is administered at a frequency of once a week, and a checkpoint inhibitor is administered at a frequency of twice a week. In some embodiments, BT1718, or a pharmaceutically acceptable salt thereof, is administered at a frequency of once a week, and a checkpoint inhibitor is administered at a frequency of once every 3 days.

In some embodiments, the present invention provides a method of treating a cancer in a patient, comprising administering to the patient BT1718, or a pharmaceutically acceptable salt thereof, at a dose level of about 6.4 mg/kg, and a checkpoint inhibitor at a dose level of about 10 mg/kg. In some embodiments, BT1718, or a pharmaceutically acceptable salt thereof, is administered at a frequency of once a week, and a checkpoint inhibitor is administered at a frequency of twice a week. In some embodiments, BT1718, or a pharmaceutically acceptable salt thereof, is administered at a frequency of once a week, and a checkpoint inhibitor is administered at a frequency of once every 3 days.

Exemplary Cancers

In some embodiments, the cancer is a solid tumor. In some embodiments, the cancer is associated with MT1-MMP. In some embodiments, the cancer is high MT1-MMP expressing. For example, Adley et al. have reported that MT1-MMP has a high level of expression in clear cell carcinomas of the ovary (Adley et al. "Expression of Membrane Type 1 Matrix Metalloproteinase (MMP-14) in Epithelial Ovarian Cancer: High Level Expression in Clear Cell Carcinoma" *Gynecol Oncol*. 2009 February; 112(2): 319-324).

In some embodiments, the cancer is bladder cancer. In some embodiments, the bladder cancer is selected from the group consisting of basal, p53-like, and luminal.

In some embodiments, the cancer is endometrial cancer. In some embodiments, the endometrial cancer is selected from the group consisting of MMR-D, POLE EDM, p53 WT, p53 abnormal, Type I, Type II, carcinoma, carcinosarcoma, endometrioid adenocarcinoma, serous carcinoma, clear cell carcinoma, mucinous carcinoma, mixed or undifferentiated carcinoma, mixed serous and endometrioid, mixed serous and low-grade endometrioid, and undifferentiated.

In some embodiments, the cancer is esophageal cancer. In some embodiments, the esophageal cancer is selected from the group consisting of adenocarcinoma (EAC), squamous cell carcinoma (ESCC), chromosomal instability (CIN), Epstein-Barr virus (EBV), genomically stable (GS), and microsatellite instability (MSI).

In some embodiments, the cancer is glioblastoma. In some embodiments, the glioblastoma is selected from the group consisting of proneural, neural, classical, and mesenchymal.

In some embodiments, the cancer is mesothelioma. In some embodiments, the mesothelioma is selected from the group consisting of pleural mesothelioma, peritoneal mesothelioma, pericardial mesothelioma, epithelioid mesothelioma, sarcomatoid mesothelioma, biphasic mesothelioma, and malignant mesothelioma.

In some embodiments, the cancer is multiple myeloma. In some embodiments, the multiple myeloma is selected from the group consisting of hyperdiploid, non-hyperdiploid, cyclin D translocation, MMSET translocation, MAF translocation, and unclassified.

In some embodiments, the cancer is ovarian cancer. In some embodiments, the ovarian cancer is selected from the group consisting of clear cell, endometrioid, mucinous, high-grade serous and low-grade serous ovarian cancer.

In some embodiments, the cancer is pancreatic cancer. In some embodiments, the pancreatic cancer is selected from the group consisting of squamous, pancreatic progenitor, immunogenic, and ADEX (Aberrantly Differentiated Endocrine eXocrine) pancreatic cancer.

In some embodiments, the cancer is prostate cancer. In some embodiments, the prostate cancer is selected from the group consisting of AZGP1 (subtype I), MUC1 (subtype II), and MUC1 (subtype III) prostate cancer.

Co-Administration of BT1718 and a Checkpoint Inhibitor

BT1718, or a pharmaceutically acceptable salt thereof, may be administered separately from a checkpoint inhibitor, as part of a multiple dosage regimen. Alternatively, BT1718, or a pharmaceutically acceptable salt thereof, and a checkpoint inhibitor may be mixed together in a single composition. If administered as a multiple dosage regimen, BT1718, or a pharmaceutically acceptable salt thereof, and a checkpoint inhibitor may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, BT1718, or a pharmaceutically acceptable salt thereof, and a checkpoint inhibitor are administered as a multiple dosage regimen within greater than 24 hours apart.

As used herein, the term "combination," "combined," and related terms refers to the simultaneous or sequential administration of therapeutic agents in accordance with this invention. For example, BT1718, or a pharmaceutically acceptable salt thereof, may be administered with a checkpoint inhibitor simultaneously or sequentially in separate unit dosage forms or together in a single unit dosage form. Accordingly, the present invention provides a single unit dosage form comprising BT1718, or a pharmaceutically acceptable salt thereof, a checkpoint inhibitor, and optionally a pharmaceutically acceptable carrier, adjuvant, or vehicle.

The amount of BT1718, or a pharmaceutically acceptable salt thereof, and a checkpoint inhibitor that may be combined with the carrier materials to produce a single dosage form will vary depending upon the host treated and the particular mode of administration. Preferably, a composition of the invention should be formulated so that a dosage of between 0.01-100 mg/kg body weight/day of a compound of the invention can be administered.

BT1718, or a pharmaceutically acceptable salt thereof, and a checkpoint inhibitor may act synergistically. Therefore, the amount of BT1718, or a pharmaceutically acceptable salt thereof, and a checkpoint inhibitor in such compositions may be less than that required in a monotherapy utilizing only that therapeutic agent.

The amount of a checkpoint inhibitor present in the compositions of this invention may be no more than the amount that would normally be administered in a composition comprising it as the only active agent. Preferably the amount of a checkpoint inhibitor in the presently disclosed compositions will range from about 50% to 100% of the amount normally present in a composition comprising that agent as the only therapeutically active agent. In some embodiments, a checkpoint inhibitor is administered at a dosage of about 50%, about 55%, about 60%, about 65%, about 70%, about 75%, about 80%, about 85%, about 90%, or about 95% of the amount normally administered as monotherapy. As used herein, the phrase "normally administered" means the amount an FDA approved therapeutic agent is approved for dosing per the FDA label insert.

The pharmaceutical compositions of this invention may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

5. Exemplary Checkpoint Inhibitors

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, a checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, a checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, a checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, a checkpoint inhibitor is selected from nivolumab, pembrolizumab, ipilimumab, avelumab, durvalumab, atezolizumab, or pidilizumab.

EXEMPLIFICATION

The following Examples illustrate the invention described above; they are not, however, intended to limit the scope of the invention in any way. The beneficial effects of the pharmaceutical compounds, combinations, and compositions of the present invention can also be determined by other test models known as such to the person skilled in the pertinent art.

Example 1

In Vivo Efficacy Test of BT1718 Alone or in Combination with Anti-Pd-1 Antibody in the Treatment of 3LL Syngeneic Model in C57BL/6 Mice Study Objective The objective of the research was to evaluate the in vivo anti-tumor efficacy of BT1718 alone or in combination with Anti-PD-1 antibody in the treatment of the subcutaneous 3LL syngeneic model in C57BL/6 mice.

Experimental Design

Materials
Animals
  Species: *Mus Musculus*
  Strain: C57BL/6 mice
  Age: 6-10 weeks
  Sex: Female
  Body weight: 18-22 g
  Number of animals: 36 plus spare
Housing Condition
  The animals were kept in ventilation cages at constant temperature and humidity with 3 animals in each cage.
  Temperature: 20~26° C.
  Humidity: 40-70%.
  Cages: Made of polycarbonate. The size is 300 mm×180 mm×150 mm. The bedding material is corn cob, which was changed twice per week.
  Diet: Animals had free access to irradiation sterilized dry granule food during the entire study period.
  Water: Animals had free access to sterile drinking water.
  Cage identification: The identification labels for each cage contained the following information: number of animals, sex, strain, the date received, treatment, study number, group number and the starting date of the treatment.
  Animal identification: Animals were marked by ear coding.
Test and Positive Control Articles
  Product identification: BT1718
  Physical description: Lyophilized powder
  Package and storage condition: stored at −80° C.
  Product identification: Anti-PD-1 antibody
  Physical description: Liquid
  Concentration: 11.5 mg/ml
  Package and storage condition: stored at −80° C.
Experimental Methods and Procedures
Cell Culture
  The 3LL tumor cells were maintained in vitro as a monolayer culture in medium supplemented with 10% heat inactivated fetal bovine serum at 37° C. in an atmosphere of 5% $CO_2$ in air. The tumor cells were routinely subcultured twice weekly by trypsin-EDTA treatment. The cells growing in an exponential growth phase will be harvested and counted for tumor inoculation.
Tumor Inoculation
  Each mouse was inoculated subcutaneously at the right flank with 3LL tumor cells ($1×10^6$) in 0.1 ml of PBS for tumor development. The animals were randomized and treatment was started when the average tumor volume reaches approximately 105 $mm^3$ for the efficacy study. The test article administration and the animal numbers in each group were shown in the experimental design table (Table 1.1).
Testing Article Formulation Preparation

TABLE 1.1

Experimental design

| Gr | n | I/O | Dose (mg/kg) | frequency | compound | Dose (mg/kg) | frequency |
|---|---|---|---|---|---|---|---|
| 1 | 6 | Vehicle | — | biw*2 weeks | Vehicle | — | biw*2 weeks |
| 2 | 6 | Vehicle | — | biw*2 weeks | BT1718 | 3 | biw*2 weeks |
| 3 | 6 | Vehicle | — | biw*2 weeks | BT1718 | 10 | biw*2 weeks |
| 4 | 6 | aPD-1 | 10 | biw*2 weeks | Vehicle | — | biw*2 weeks |
| 5 | 6 | aPD-1 | 10 | biw*2 weeks | BT1718 | 3 | biw*2 weeks |
| 6 | 6 | aPD-1 | 10 | biw*2 weeks | BT1718 | 10 | biw*2 weeks |

| Test article | Con. (mg/ml) | Formulation | Buffer |
|---|---|---|---|
| Vehicle1 | — | 25 mM Histidine pH7, 10% Sucrose | — |
| Vehicle2 | — | 20 mM Histidine pH5, 5% Sucrose | — |
| BT1718 | 1.0 | Add 10 mg BT1718 into 10 ml buffer, sonicate and shake to ensure the solution to be clear | 25 mM Histidine pH7, 10% Sucrose |
|  | 0.3 | Add 900 ul 1.0 mg/ml BT1718 into 2.1 ml buffer, shake to ensure the solution to be clear |  |
|  | 0.1 | Add 300 ul 1.0 mg/ml BT1718 into 2.7 ml buffer, shake to ensure the solution to be clear |  |

-continued

| Test article | Con. (mg/ml) | Formulation | Buffer |
|---|---|---|---|
| PD-1 | 1 | Add 348 ul 11.5 mg/ml PD-1 into 3.652 ml buffer, shake to ensure the solution to be clear | 20 mM Histidine pH5, 5% Sucrose |

Observations

All the procedures related to animal handling, care and the treatment in the study were performed according to the guidelines of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured every day), eye/hair matting and any other abnormal effect as stated in the protocol. Death and observed clinical signs were recorded on the basis of the numbers of animals within each subset.

Tumor Measurements and the Endpoints

The major endpoint was to see if the tumor growth could be delayed or mice could be cured. Tumor size was measured three times weekly in two dimensions using a caliper, and the volume was expressed in $mm^3$ using the formula: $V=0.5 \, a \times b^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.

TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Statistical Analysis

Summary statistics, including mean and the standard error of the mean (SEM), are provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using Prism. $P<0.05$ was considered to be statistically significant.

Results

The body weight curve is depicted in FIG. 1.

Figure 2:
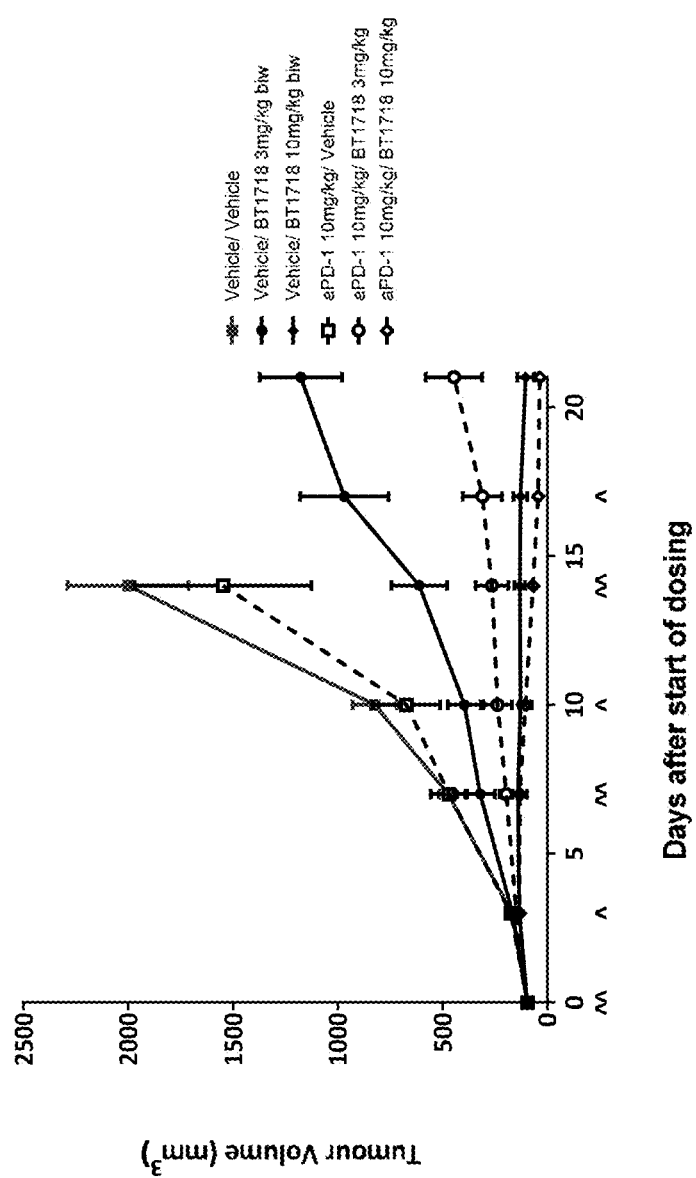
FIG. 2 depicts the tumor volume trace after administering BT1718 and PD-1 to the C57BL/6 mice bearing 3LL tumor. Data points represent group mean, error bars represent standard error of the mean (SEM).

The tumor growth curve is shown in FIG. 2.

Tumor Volume Trace

Mean tumor volume over time in female C57BL/6 mice bearing 3LL is shown in Table 1.2.

TABLE 1.2

Tumor volume trace over time

| | | Days after the start of treatment | | | | | | |
|---|---|---|---|---|---|---|---|---|
| Gr. | Treatment | 0 | 3 | 7 | 10 | 14 | 17 | 21 |
| 1 | Vehicle, ip, biw + Vehicle, iv, biw | 96 ± 9 | 170 ± 14 | 474 ± 44 | 825 ± 105 | 2001 ± 289 | | |
| 2 | Vehicle, ip, biw + BT1718, 3 mpk, iv, biw | 96 ± 7 | 167 ± 29 | 320 ± 71 | 396 ± 79 | 612 ± 133 | 968 ± 211 | 1177 ± 196 |
| 3 | Vehicle, ip, biw + BT1718, 10 mpk, iv, biw | 96 ± 6 | 134 ± 17 | 141 ± 18 | 128 ± 16 | 132 ± 26 | 129 ± 33 | 104 ± 41 |
| 4 | PD-1, 10 mpk, ip, biw + Vehicle, iv, biw | 96 ± 6 | 175 ± 14 | 470 ± 87 | 672 ± 161 | 1549 ± 423 | | |
| 5 | PD-1, 10 mpk, ip, biw BT1718, 3 mpk, iv, biw | 96 ± 9 | 148 ± 17 | 196 ± 31 | 237 ± 68 | 265 ± 78 | 311 ± 93 | 447 ± 136 |
| 6 | PD-1, 10 mpk, ip, biw BT1718, 10 mpk, iv, biw | 96 ± 6 | 133 ± 13 | 133 ± 35 | 104 ± 29 | 69 ± 21 | 45 ± 17 | 36 ± 13 |

Tumor Growth Inhibition Analysis

Tumor growth inhibition rate for BT1718 and Anti-PD-1 antibody in the 3LL syngeneic model was calculated based on tumor volume measurements at day 14 after the start of treatment.

TABLE 1.3

Tumor growth inhibition analysis (T/C and TGI)

| Gr | Treatment | Tumor Volume $(mm^3)^a$ | T/C$^b$ (%) | TGI (%) | P value (vs Vehicle) | P value (vs single group) |
|---|---|---|---|---|---|---|
| 1 | Vehicle, ip, biw + Vehicle, iv, biw | 2001 ± 289 | — | — | — | |
| 2 | Vehicle, ip, biw + BT1718, 3 mpk, iv, biw | 612 ± 133 | 30.6 | 72.9 | p < 0.001 | |
| 3 | Vehicle, ip, biw + BT1718, 10 mpk, iv, biw | 132 ± 26 | 6.6 | 98.1 | p < 0.001 | |
| 4 | PD-1, 10 mpk, ip, biw + Vehicle, iv, biw | 1549 ± 423 | 77.4 | 23.7 | p > 0.05 | |
| 5 | PD-1, 10 mpk, ip, biw BT1718, 3 mpk, iv, biw | 265 ± 78 | 13.2 | 91.2 | p < 0.001 | P < 0.05 |
| 6 | PD-1, 10 mpk, ip, biw BT1718, 10 mpk, iv, biw | 69 ± 21 | 3.4 | 101.4 | p < 0.001 | P > 0.05 |

$^a$Mean ± SEM.
$^b$Tumor Growth Inhibition is calculated by dividing the group average tumor volume for the treated group by the group average tumor volume for the control group (T/C).

Summary and Discussion

In this study, the in vivo anti-tumor efficacy of BT1718 alone or in combination with Anti-PD-1 antibody in 3LL syngeneic model in C57BL/6 mice was evaluated. The measured body weights are shown in the FIG. 1. Tumor volume of all treatment groups at various time points are shown in Tables 1.2 and 1.3 and FIG. 2.

The mean tumor volume of vehicle treated mice reached 2001 mm$^3$ on day 14 after the start of treatment. 2/6 mice showed obvious response to anti-PD-1 antibody treatment while 4/6 mice didn't show any response. BT1718 at 3 mg/kg and 10 mg/kg produced dose-dependent anti-tumor effect with tumor measured at 612 mm$^3$ (TGI=72.9%, p<0.001) and 132 mm$^3$ (TGI=98.1%, p<0.001). Anti-PD-1 antibody in combination with BT1718 at 3 mg/kg and 10 mg/kg further improved the therapeutic effect of BT1718, and tumors were measured at 265 mm$^3$ (TGI=91.2%, p<0.001 vs vehicle; p<0.05 vs BT1718 3 mg/kg) and 69 mm$^3$ (TGI=101.4%, p<0.001 vs vehicle; p>0.05 vs BT1718 10 mg/kg) respectively.

In this study, all mice maintained their bodyweight well.

Example 2

In Vivo Efficacy Study of Test Articles in Treatment of 3LL (LLC) Syngeneic Model Study Purpose The objective of the project is to evaluate the in vivo therapeutic efficacy of test articles in treatment of 3LL (LLC) syngeneic model in C57BL/6J mice.

Study Design

Cell Culture:

The 3LL tumor cells will be maintained in medium supplemented with 10% heat inactivated fetal bovine serum at 37° C. in an atmosphere of 5% $CO_2$ in air. The tumor cells will be routinely subcultured twice weekly. The cells growing in an exponential growth phase will be harvested and counted for tumor inoculation.

Animals:

C57BL/6J, female, 6-8 weeks, weighing approximately 18-22 g.

Tumor Inoculation:

Each mouse will be inoculated subcutaneously at the right flank with 3LL tumor cells (2*10$^6$) for tumor development. The animals will be randomized and treatment will be started when the average tumor volume reaches approximately 80-100 mm$^3$. The test article administration and the animal numbers in each group are shown in the following experimental design table.

Experimental Design.

| Group | Treatment | Dose (mg/kg) | N | Dosing Route | Schedule |
|---|---|---|---|---|---|
| 1 | Vehicle | - | 10 | iv | biw * 4 weeks |
| 2 | BT1718 | 4.8 | 10 | iv | qw * 4 weeks (2 weeks single dose + 2 weeks combo with anti-PD1) |
| 3 | Anti-PD-1 | 10 | 10 | ip | biw*4 weeks (2 weeks single dose + 2 weeks combo with BT1718) |
| 4 | BT1718 + Anti-PD-1 | 4.8 +10 | 10 | iv + ip | qw * 4 weeks + biw * 4 weeks |

Note:
IV/IP injection: The injection volume of each mouse is 10 ml/kg.
Extending Observation: 2 weeks extension for Group 2, 3, 4 after 28 days treatment
Schedule Change: Group 2, 3 would be added with Anti-PD-1 or BT1718 when vehicle group TV reach to 2000 mm$^3$ (about 2 weeks post the first dosing)

Animal Housing:

An acclimation period of approximately one week will be allowed between animal arrival and tumor inoculation in order to accustom the animals to the laboratory environment. The mice will be maintained in a special pathogen-free environment and in individual ventilation cages (5 mice per cage). All cages, bedding, and water will be sterilized before use. When working in the mouse room, the investigators will wear lab coat and latex or vinyl gloves. Each cage will be clearly labeled with a cage card indicating number of animals, sex, strain, date received, treatment, study number, group number, and the starting date of the treatment. The cages with food and water will be changed twice a week. The targeted conditions for animal room environment and photoperiod will be as follows:

Temperature 20~26° C.
Humidity 40~70%
Light cycle 12 hours light and 12 hours dark Dietary Materials:

All animals will have free access to a standard certified commercial laboratory diet. Maximum allowable concentrations of contaminants in the diet are controlled and routinely analyzed by the manufacturers. Autoclaved municipal tap water, suitable for human consumption will be available to the animals ad libitum. It is considered that there are no known contaminants in the dietary materials that could influence the tumor growth.

Assignment to Groups:

Before commencement of treatment, all animals will be weighed and the tumor volumes will be measured. Since the tumor volume can affect the effectiveness of any given treatment, mice will be assigned into groups using randomized block design based upon their tumor volumes. This ensures that all the groups are comparable at the baseline.

Observations:

The protocol and any amendment(s) or procedures involving the care and use of animals in this study will be reviewed and approved by the Institutional Animal Care and Use Committee (IACUC). During the study, the care and use of animals will be conducted in accordance with the regulations of the Association for Assessment and Accreditation of Laboratory Animal Care (AAALAC). After inoculation, the animals will be checked for morbidity and mortality. At the time of routine monitoring, the animals will be checked for any effects of tumor growth and treatments on normal behavior such as mobility, food and water consumption, eye/hair matting and any other abnormal effect. Death and observed clinical signs will be recorded on the basis of the numbers of animals within each subset.

The tumor volume will be expressed in mm3 using the formula: $V=0.5 \: a \times b^2$ where a and b are the long and short diameters of the tumor, respectively.

Termination:

1) Bodyweight Loss:

Any animal exhibiting 20% bodyweight loss at any one day will be humanely killed or the veterinary staff will be contacted.

2) Tumor Burden:

Tumor burden should not exceed 10% of the animal's bodyweight. The study will be terminated with all animals being sacrificed when the mean tumor volume of the vehicle control group reaches a value of 2,000 mm$^3$.

Ulceration: If tumor ulceration occurs, the following procedures will apply:

Animals with ulcerated tumors will be monitored at least 3 times per week with increasing frequency, up to daily, depending upon clinical signs.

Ulcerated tumors, which have not scabbed over, should be cleaned with an appropriate wound cleansing solution (e.g., Novalsan). Antibiotic cream is to be applied to the ulceration/lesion only if directed by the Veterinary staff.

Criteria for euthanasia include if the lesion:

Does not heal or form a scab within 1 week.

Is greater than 5 mm diameter.

Becomes cavitated.

Develops signs of infection (such as presence of pus) or bleeding, or if the animal shows signs of discomfort (e.g. excessive licking and biting directed at the site) or systemic signs of illness (lethargy, decreased activity, decreased food consumption, decreased body condition or weight loss). Contact the veterinary staff to discuss any possible exceptions.

3) Clinical Signs:

Animals must be euthanized if they found to be moribund (unless special permission is granted by the IACUC based on adequate justification, which must be included in the protocol and increased supportive care provided such as warm SQ fluids, Diet Gel food cup next to animal so they can reach food, cage on a warming pad for supplemental heat, etc. Note: a moribund condition indicates an animal is unlikely to survive.) For questions regarding these endpoints, please contact the Veterinary Staff.

Clinical examples of morbidity may include:

Hunched.

Persistent recumbency and lack of response to handling or other stimuli.

Signs of severe organ or system failure.

Emaciation.

Hypothermia.

CNS deficits: convulsions.

Respiratory: rapid respiratory rate, labored breathing, coughing, rales.

GI: diarrhea lasting >2 days, jaundice

Any animal that exhibits the above clinical issues will be humanely sacrificed by $CO_2$. Necropsy will not be performed in the event of an unexpected death.

Number of animals: 27 mice plus spare Note:

For efficacy or tolerability/MTD studies, severe clinical observations and BWL (Bodyweight loss) of enrolled animals will be recorded in the data update files which will be sent to study PI three times per week, more than 10%, 15% and 20% BWL from the first measurement will be labeled in different colors.

Diet-gel should be provided to a cage that houses any animals with more than 10% BWL.

Information of Test Articles

BT1718: Lyophilised powder; package and storage condition: −80° C.

Formulation of Vehicles and TAs:

| Compound | Conc. (mg/ml) | Formulation |
|---|---|---|
| Vehicle | — | 25 mM Histidine, 10% sucrose, pH7 |
| BT1718 | 0.48 | dissolve the powder with Histidine buffer |
| Anti-PD-1 antibody | 1 | Dilute the PD-1 Ab with saline |

Figure 3:
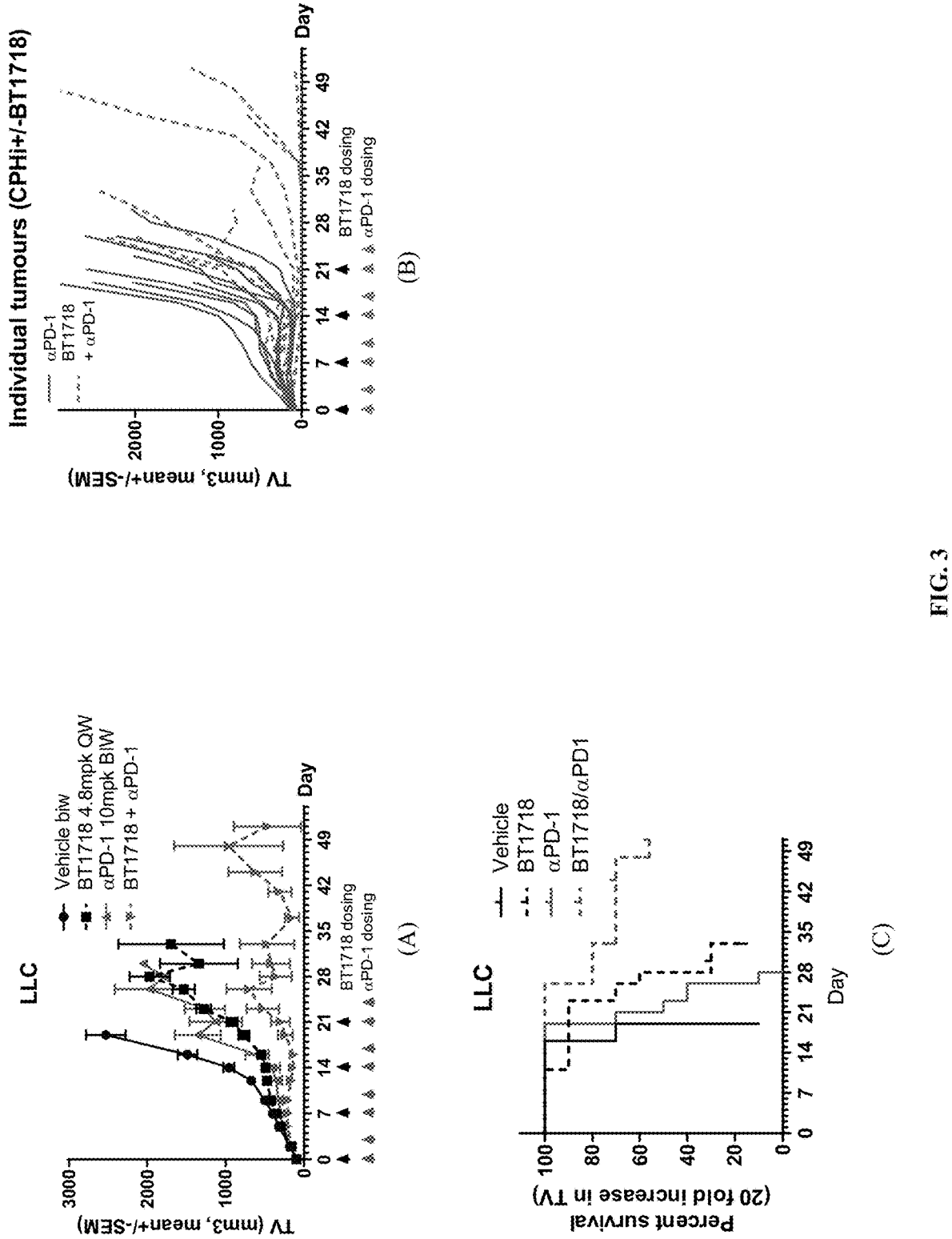
FIG. 3 depicts the tumor volume trace and percentage survival (defined as 20-fold increase in tumor volume) after administering BT1718 and PD-1 to the C57BL/6J mice bearing 3LL tumor. Data points represent group mean, error bars represent standard error of the mean (SEM). Survival rates in BT1718/checkpoint inhibitor combination arms are vastly improved compared to each of the single agent treatments

The antitumor activity and percentage survival are shown in FIG. 3. Survival rates in BT1718/checkpoint inhibitor combination arms are vastly improved compared to each of the single agent treatments.

Example 3

Efficacy Evaluation of BT17BDC-18 Alone and in Combination with Anti-MPD-1 Against Established Orthotopic E0771 Murine Mammary Carcinoma in Female C57BL/6 Mice The purpose of this study was to evaluate the anti-cancer activity of BT17BDC-18 alone and in combination with anti-mPD-1 against established orthotopic E0771 murine mammary carcinoma in female C57BL/6 mice.

Test Agents and Vehicles

BT17BDC-18:

Physical description: Clear, colorless solution; Concentration: 0.96 mg/ml; Storage condition: −80° C.

Vehicle: 25 mM Histidine/10% sucrose in water;

High Dose Formulation 0.62 mg/ml; Formulation pH: 6.6; Formulation description: Clear, colorless solution; Dose volume 0.2 ml/20 g; Storage: Dosed promptly after formulation Note:

Groups 2 & 6 were dosed at 6.2 mg/kg

Groups 3 & 7 were dosed at 4.8 mg/kg

To prepare the 6.2 mg/kg dosage level of BT17BDC-18, the 0.96 mg/ml stock solution was diluted by adding 2.125 ml of the vehicle to 3.875 ml of the 0.96 mg/ml stock solution to achieve a 0.62 mg/ml solution To prepare the 4.8 mg/kg dosage level of BT17BDC-18, the 0.96 mg/ml stock solution was diluted 1:1 with the vehicle to achieve a 0.48 mg/ml solution.

Paclitaxel:

White, hygroscopic powder; storage: −20° C.; Vehicle: 10% EtOH/10% Cremaphor/80% Saline; High Dose Formulation: 1.5 mg/ml; Formulation pH: 5.5; Formulation description: Clear, colorless solution; Storage: Dosed promptly after formulation; Dose volume 0.2 ml/20 g anti-mouse PD-1 (clone: RMP1-14):

Physical description: Clear, colorless solution; Concentration: 7.24 mg/ml; Storage: 4° C., protected from light; Vehicle: Phosphate buffered saline (PBS); High Dose Formulation: 1 mg/ml; Formulation: pH 7.3; Formulation description: Clear, colorless solution; Storage: 4° C.; Dose volume: 0.2 ml/20 g Animals and Husbandry All procedures carried out in this experiment were conducted in compliance with the applicable laws, regulations and guidelines of the National Institutes of Health (NIH) and with the approval of MI Bioresearch's Animal Care and Use Committee. MI Bioresearch is an AAALAC accredited facility.

| | | | |
|---|---|---|---|
| Species | Mouse | | |
| Strain | C57BL/6 mice (C57BL/6J) | Gender | Female |
| Age at implant | 6-7 weeks | On Study/Total | 76/152 |
| Diet | Teklad 2918.15 Rodent Diet | Water | Ad libitum |
| Supplements | NA | Fasting | NA |

-continued

| | | | |
|---|---|---|---|
| Acclimation | 9 days | Housing | Innovive disposable ventilated caging with corn cob bedding inside Biobubble ® Clean Rooms |
| Animals/cage | 4 mice | Light cycle | 12/12 h |
| Temp | 70 ± 2° F. | Humidity | 30-70% |
| ID method | Ear punch | Weigh freq | 3x/week |
| Measure freq | 3x/week | Mean Wt (D15) | 19.2 g (range of group means, 18.5-19.6 g) |
| Min Weight (D15) | 16.6 g | Surgeries | NA |
| Staged at | 105 mm$^3$ (range of group means, 102-107mm$^3$), Day 15 | Euthanized at | Tumor volume >2000 mm$^3$, or client requested study termination (Day 60) |
| Necropsy | Yes | Health Checks | Daily |
| Comments | Group 9 was not included in the tumor volumes at staging due to the enrollment criteria being different for that group. Group 9 was added for sample collection, 6 tumors <250 mm$^3$ and another 6 tumors >500 mm$^3$. | | |

Cell Preparation/Implantation

| | | | |
|---|---|---|---|
| Model | E0771 | Histotype | Murine mammary carcinoma |
| | | Implant type | Cells |
| Media | RPMI 1640 Medium modified with 1 mM Na pyruvate, 10 mM HEPES buffer, 2.8 ml 45% glucose (1.25 g) and 1% GlutaMAX (Gibco) and supplemented with 10% Non-Heat-Inactivated Fetal Bovine Serum (FBS) and 1x Penicillin/Streptomycin/L-Glutamine (PSG) | Dissociation solution | 0.25% Trypsin/ 2.21 mM EDTA in HBSS |
| Route | Orthotopic | Location | Mammary fat pad #4 |
| Inoculum | 1.0E+06 trypan-excluding cells | Implant media | Serum-free RPMI 1640 Medium |
| Matrigel | NA | Inj. Volume | 50 µL |
| Viability (pre) | 94% | Viability (post) | 91% |
| Comments | Mice were lightly anesthetized via inhalation of isoflurane/ oxygen and the hair over the implantation site was shaved using electric clippers 48 hours prior to implant. The mice were also lightly anesthetized for tumor implants. | | |

Treatment

All mice were sorted into study groups based on caliper estimation of tumor burden. The mice were distributed to ensure that the mean tumor burden for all groups was within 10% of the overall mean tumor burden for the study population.

| Group | N | Treatment | Dose | ROA | Regimen | Days of treatment |
|---|---|---|---|---|---|---|
| 1 | 8 | Vehicle Control | 0.2 ml/20 g | IV | Q7Dx4 | Days 15, 22, 29, and 36 |
| 2 | 8 | BT17BDC-18 | 6.2 mg/kg | IV | Q7Dx4 | Days 15, 22, 29, and 36 |
| 3 | 8 | BT17BDC-18 | 4.8 mg/kg | IV | Q7Dx4 | Days 15, 22, 29, and 36 |
| 4 | 8 | Paclitaxel | 15 mg/kg | IV | Q7Dx4 | Days 15, 22, 29, and 36 |
| 5 | 8 | anti-mPD-1 | 10 mg/kg | IP | (Q3Dx2; 2off)x2 | Days 15, 18, 21, and 24 |
| 6 | 8 | BT17BDC-18 + anti-mPD-1 | 6.2 mg/kg + 10 mg/kg | IV + IP | Q7Dx4 + (Q3Dx2; 2off)x2 | Days 15, 22, 29, and 36 + Days 15, 18, 21, and 24 |
| 7 | 8 | BT17BDC-18 + anti-mPD-1 | 4.8 mg/kg + 10 mg/kg | IV + IP | Q7Dx4 + (Q3Dx2; 2off)x2 | Days 15, 22, 29, and 36 + Days 15, 18, 21, and 24 |
| 8 | 8 | Paclitaxel + anti-mPD-1 | 15 mg/kg + 10 mg/kg | IV + IP | Q7Dx4 + (Q3Dx2; 2off)x2 | Days 15, 22, 29, and 36 + Days 15, 18, 21, and 24 |
| 9 | 12 | Untreated | NA | NA | NA | NA |

Sampling

| Group(s) | Animals | Tissue (s) | Time Pts | Product | Description |
|---|---|---|---|---|---|
| 9 | 1-12 | Tumor | Tumor volume <250 mm$^3$ and >500 mm$^3$ | Tumor snap frozen or FFPE blocks | 6 tumors collected at small sizes (<250 mm$^3$) and the other 6 tumors collected at larger sizes (>500 mm$^3$) and processed. |

Comments: From each tumor range, 3 tumors were placed in 10% NBF, fixed for 24-48 hours and then processed into FFPE blocks. The other 3 tumors were snap frozen in liquid nitrogen and stored at −80° C. (See Appendix 9)

Pharmacology and Imaging Endpoints

| Data Type | Method | Primary Endpoint 1 | Primary Endpoint 2 | Primary Endpoint 3 |
|---|---|---|---|---|
| Pharmacology | Caliper Scale and clinical observations | Time to progression Treatment related weight change (%) | Median ΔT/ΔC (Day 36) Treatment related death (%) | % CR, PR, and TFS |

Results

Tumor Growth/General Observations/Controls

The mean estimated tumor burden for all groups in the experiment on the first day of treatment was 105 mm$^3$, and all of the groups in the experiment were well-matched (range of group means, 102-107 mm$^3$). All animals weighed at least 16.6 g at the initiation of therapy. Mean group body weights at first treatment were also well-matched (range of group means, 18.5-19.6 g). A tumor burden of 2000 mm$^3$, was chosen for evaluation of efficacy by time to progression (time to euthanasia/death).

In the Control Group, the median time to progression was 22.3 days, and the median tumor volume doubling time was 4.9 days. Control animals experienced a 1.7 g (9.5%) mean weight gain during the treatment regimen. There were no spontaneous regressions in the Control Group. All thioglycolate cultures of cells used for implantation of this study were negative for gross bacterial contamination.

All of this information in consistent with historical norms and the experiment was judged to be technically satisfactory and the data appropriate for evaluation.

Glossary

Day 0—The day on which the tumors are implanted (not to be confused with the 1st day of treatment which is always indicated relative to Day 0).

Treatment related deaths (%)—An animal is presumed to experience a treatment-related death if it is found dead or is euthanized in moribund condition during or within two weeks after the last treatment with a tumor burden less than half that of the smallest lethal tumor in the control group, and only if the animal shows no evidence of infection, mechanical dosing trauma, or other obvious causes of morbidity at necropsy. Animals euthanized during the same period for other causes (sampling, accidental trauma, etc.) are excluded from this calculation. This designation is meant to help identify animals that may have experienced drug induced toxicity, but it does not directly imply causality. (Group toxicity parameter)

Treatment-related weight change—This is a group endpoint calculated from the group mean body weights. It is calculated differently for specific circumstances as follows:

If (at any point between the first day of treatment and two weeks after the final treatment) the mean group body weight decreases by more than 2%, the maximum weight loss is reported, even if body weight eventually rebounded during treatment to a net weight gain. In the special case of a rebound to a net gain, the recovery is thoroughly noted in the results section.

If mean group body weights do not decrease by more than 2% at any point, the body weight change is reported as the difference between the body weight on the first day of treatment and the date that is two weeks after the end of treatment.

Note that the duration of treatment can vary by group, so direct comparison of weight gains (in particular) needs to account for that.

When weight loss occurs, in models that typically have tumor progression induced weight loss, multiple factors influence body weight change. To assess the contribution of test agents to weight loss, Net Treatment Related Weight Loss may be used. This is done in two different ways depending on the degree of efficacy observed in the study.

When no efficacy is apparent, Net weight loss is calculated by subtracting the mean weight loss in the control group from the mean weight loss in the treated group for every day of the study.

When efficacy is observed, widely differing tumor burdens can occur between the control and treated groups. When this occurs, net weight loss is calculated by normalizing for tumor burden. We do this by constructing a plot of control group mean tumor burden vs control group mean weight loss, using all of the weight data available for the control group. (Typically log/linear plots of tumor burden vs weight loss are easiest to use.) On any given study day, the net weight loss of the treated group is estimated by looking up the mean tumor burden of the treated group on the control group reference plot and reading off the implied/expected weight loss due to tumor burden. This value is then subtracted from the mean weight loss in the treated group to generate the net weight loss for the treated group on that day. The calculated net weight loss is then used to estimate the tolerance to the drug.

Efficacy

ΔC and ΔT—Are individual mouse endpoints that are calculated for each mouse as follows:

$$\Delta T = T_t - T_0 \text{ and } \Delta C = C_t - C_0,$$

Where $T_t$ and $T_0$ are the tumor burdens of a treated mouse at time t or at the initiation of dosing, respectively. ΔC reflects similar calculations for the control mice.

Median ΔT/ΔC—Is a group endpoint. It is calculated for each day of treatment as:

$$\text{Median}\frac{\Delta T}{\Delta C} = \left(\frac{\Delta T_{med}}{\Delta C_{med}}\right) * 100 = \left(\frac{\text{median}(T_t - T_0)}{\text{median}(C_t - C_0)}\right) * 100$$

The results are presented as a %. When the median ΔT/ΔC is negative (the median treated tumor burden is regressing), the median ΔT/ΔC is not reported and the Median % Regression is reported instead.

% Regression—Is a group endpoint. It indicates the percentage reduction in the Median tumor volume from baseline. It is calculated as:

$$\% \text{ Regression} = -\left(\frac{\Delta T_{med}}{T_0 med}\right) * 100$$

Time to Evaluation Size (TES)—TES is an individual mouse endpoint and it is expressed in days from tumor implant. It is the time it takes the tumor burden to reach a specified value, and it can be calculated from any method of evaluating tumor burden (caliper measurements, BLI, anatomical imaging, etc.). It is calculated by log-linear interpolation between the two closest data points that bracket the chosen tumor burden.

$$D_{ES} = D_h - \frac{((\log V_h - \log ES) * (D_h - D_l))}{(\log V_h - \log V_l)}$$

where:
$D_{ES}$=TES$_i$—the day evaluation size is reached
$D_h$—the day of the first measurement greater than the ES was reached
$D_l$—the day of the last measurement before the ES was reached
$V_h$—The tumor volume on day $D_h$
$V_l$—the tumor volume on $D_l$
ES—the evaluation size Time to Progression (TP)—Time to progression is a surrogate for lifespan, time on study, or lifespan. It is used for studies that involve IACUC mandated euthanasia of animals for excessive tumor burdens (even if the animals otherwise appear normal). The mandated tumor burden limit is tumor model dependent. TP data is analyzed by Kaplan Meier methods just as traditional life span data. The Time to Progression for an individual animal is the number of days between initiation of treatment and the death or required euthanasia of that animal. (The day of first treatment is the day of first treatment in the study as a whole and is not specific to the group in question.) When euthanasia is prompted for excessive tumor burden (typically >2000 mm3, but model dependent), the day of euthanasia is calculated from a log-linear interpolation between the adjacent data points on either side of the tumor burden limit, not from the actual day of euthanasia. This puts all animals on the same footing, and removes the impact of possibly delayed euthanasia (which may occur for sampling, or weekends and holidays). Animals euthanized for scheduled sampling or other causes unrelated to disease progression or therapy are excluded from this calculation. The median Time to Progression for a group is used to calculate the % Increase in Time to Progression (% ITP). Note that Lifespan and Time to Progression are mutually exclusive endpoints and cannot be used in the same study. In addition, TES and TP are not identical even if the Evaluation Size chosen for each is identical. They differ in that TP includes animals that die (of nonextraneous causes) during the study without ever reaching the chosen ES, thereby rendering a more balanced depiction of the therapeutic outcome.

% Increase in Time to Progression (% ITP)—% ITP is a group endpoint. It is calculated as:

$$\% \text{ ITS} = \left\{\frac{[(\text{median Treated } TP) - (\text{median Control } TP)]}{\text{median Control } TP}\right\} * 100$$

Tumor doubling time (Td)–Td is an individual and group parameter, typically expressed as the median Td of the group. It is measured in days. Td can be calculated from any type of volumetric data (caliper measurements, BLI signals, etc). For QC purposes it is calculated for the exponential portion of the tumor growth curve. Data points during any lag phase and in the Gompertzian advanced stage are not included. Typical tumor burden limits are between 100 and 1000 mm3, but actual selection is data driven. Td is calculated for each mouse from a least squares best fit of a log/linear plot of tumor burden vs day as:

$Td = \log 2/\text{slope}$

On rare occasions the median Td is used as a potential indicator of efficacy. As such it is calculated as the median for every group, over a specified range of days thought to reflect a period of response to therapy.

Tumor Regressions

Complete Regression (CR)—An animal is credited a complete regression if its tumor burden is reduced to an immeasurable volume at any point after the first treatment. Our convention is to record any tumor measurement less than 5 mm as a "0." The CR must be maintained for at least 2 consecutive measurements. This is in keeping with the convention of the NCI and reflects the inherent and unacceptably high mechanical error in such measurements in addition to the uncertain biology of what is measured at those small sizes. (Individual efficacy parameter)

Partial regression—An animal is credited with a partial regression if its tumor burden decreases to less than half of the tumor burden at first treatment. The PR must be maintained for at least 2 consecutive measurements for caliper driven studies. (For BLI driven studies the required confirmation is waived because of the dynamic range of the measurements and typically longer intervals between imaging.) PRs are tabulated exclusive of CRs, thus an animal that achieves a CR is not also counted as a PR. (Individual efficacy parameter)

Tumor-free Survivor (TFS)—A TFS is any animal that (1) survives until termination of the study, and (2) has no reliably measurable evidence of disease at study termination. Mice that are tumor-free at some point during the study, but are then euthanized for sampling or other purposes prior to the end of the study are not considered TFS. They are excluded from calculation of the % TFS. TFS status does not imply "cure."

Data

Figure 4:
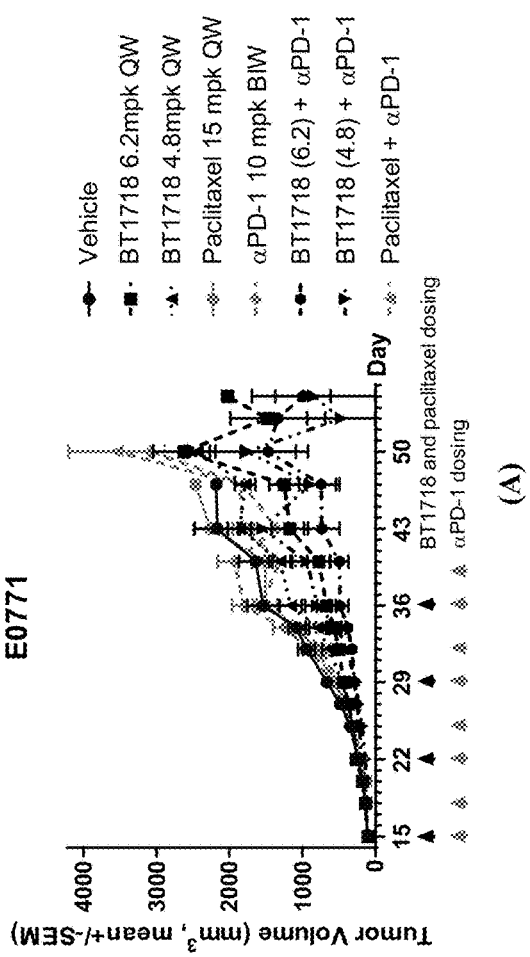
FIG. 4 depicts the tumor volume traces after administering of BT1718, paclitaxel, and PD-1 to C57BL/6 mice bearing orthotopic E0771 murine mammary carcinoma. Data points represent group mean, error bars represent standard error of the mean (SEM). Treatment with BT1718 at 6.2 mg/kg or 4.8 mg/kg in combination with anti-PD-1 at 10 mg/kg was slightly more effective than either single agent treatment, producing a 13.2 day (59.0%) and a 7.7 day (34.5%) increase in time to progression. The combination treatments resulted in a 12.5% (⅛) incidence of complete regressions in each BT1718/anti-PD-1 combination arm. Poor response was observed for Paclitaxel or aPD-1 as single agents or in combination.
Figure 4:
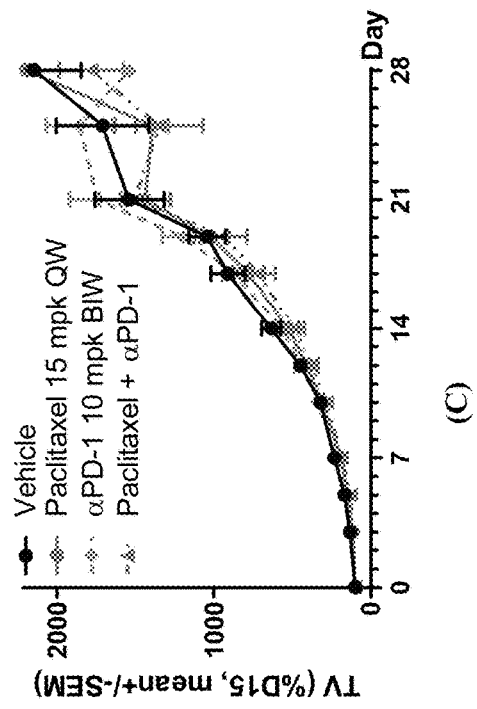
Figure 4:
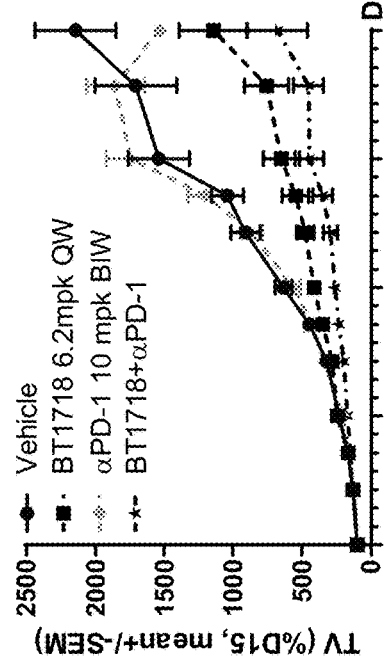

BT1718 with anti-PD-1 antibody leads to increased antitumor activity compared to monotherapies. The tumor volume traces after the treatment is shown in FIG. 4.

Overall all treatment regimens were tolerated. There were two deaths in both the Vehicle Control group as well as the single agent paclitaxel group (15 mg/kg). These deaths were considered to be non-specific deaths with necropsy observations similar to what was observed in mice with advanced disease. However, treatment cannot be completely ruled out from the cause of death. There was one death in the Vehicle Control group that occurred immediately following injection and was likely a technical dosing error.

Single agent treatment with BT17BDC-18 at 6.2 mg/kg or 4.8 mg/kg was mildly effective, producing a 10.5 day (47.1%) and a 6.6 day (29.4%) increase in time to progression and a Day 36 median $\Delta T/\Delta C$ values of 38% and 72%, respectively. Treatment with BT17BDC-18 did not produce any regressions or any tumor free survivors.

Treatment with anti-mPD-1 at 10 mg/kg was ineffective, producing a 0.2 day (0.7%) increase in time to progression and a Day 36 median $\Delta T/\Delta C$ value of 121%. The activity produced by treatment with anti-mPD-1 is consistent with MI Bioresearch's historical data.

Treatment with BT17BDC-18 at 6.2 mg/kg or 4.8 mg/kg in combination with anti-mPD-1 at 10 mg/kg was slightly more effective than either single agent treatment, producing a 13.2 day (59.0%) and a 7.7 day (34.5%) increase in time to progression and a Day 36 median $\Delta T/\Delta C$ values of 27% and 54%, respectively. The combination treatments each resulted in a 12.5% (⅛) incidence of complete regressions. The combination of BT17BDC at 6.2 mg/kg with anti-mPD-1 also resulted in a 12.5% (⅛) incidence of tumor free survivors.

Treatment with paclitaxel at 15 mg/kg was mildly active, producing a 4.0 day (17.9%) increase in time to progression and a Day 36 median $\Delta T/\Delta C$ value of 94%.

Treatment with paclitaxel at 15 mg/kg in combination with anti-mPD-1 at 10 mg/kg resulted in similar activity to paclitaxel alone, producing a 3.5 day (15.5%) increase in time to progression and a Day 36 median $\Delta T/\Delta C$ value of 94%.

Example 4

In Vivo Efficacy Study of BT1718 and Anti-CTLA4 in Treatment of CT-26 Syngeneic Model in BALB/C Mice Study Objective The objective of the research is to evaluate the in vivo anti-tumor efficacy of BT1718 and anti-CTLA4 in CT-26 syngeneic model in BALB/c mice.

Experiment Design

| Group | Treatment | n | Dose (mg/kg) | Dosing Volume (μL/g) | Dosing Route | Schedule |
|---|---|---|---|---|---|---|
| 1 | Vehicle | 10 | — | 10 | Iv | qw × 2 weeks |
| 2 | BT1718 | 10 | 6.4 | 10 | Iv | qw × 3 weeks |
| 3 | anti-CTLA4 | 10 | 10 | 10 | Ip | biw × 4 weeks |
| 4 | BT1718 + anti-CTLA4 | 10 | 6.4 + 10 | 10 | Iv + ip | qw + biw 4× weeks |

*Mice of group 3 and 4 were kept monitoring after 4 weeks' treatment, and the immune system was re-challenged with CT-26 cells on Day 62.

Materials:
Animal and Housing Conditions
Animals for Efficacy Portion
 Species: *Mus Musculus*
 Strain: BALB/C
 Age: 6-8 weeks (Efficacy), 17-20 weeks (Re-challenge)
 Sex: female
 Body weight: 18-22 g (Efficacy), 25-30 g (Re-challenge)
 Number of animals: 40 mice plus spare
Animals for Re-Challenge Control Group
 Group 5
 Species: *Mus Musculus*
 Strain: BALB/c
 Age: 19-21 weeks
 Sex: female
 Body weight: 22-26 g
 Number of animals: 10 mice
 Group 6
 Species: *Mus Musculus*
 Strain: BALB/c
 Age: 11-12 weeks
 Sex: female
 Body weight: 21-25 g
 Number of animals: 10 mice
Housing Condition The mice were kept in individual ventilation cages at constant temperature and humidity with 5 animals in each cage.
 Temperature: 20~26° C.
 Humidity 40-70%.
 Cages: Made of polycarbonate. The size is 300 mm×180 mm×150 mm. The bedding material is corn cob, which is changed twice per week.
 Diet: Animals had free access to irradiation sterilized dry granule food during the entire study period.
 Water: Animals had free access to sterile drinking water.
 Cage identification: The identification labels for each cage contained the following
 information: number of animals, sex, strain, the date received, treatment, study number, group number and the starting date of the treatment.
 Animal identification: Animals were marked by ear coding.
Test Articles
 Product identification: BT1718
 Physical description: Lyophilised powder
 Molecular weight: 3511.38
 Purity: 97.70%
 Package and storage condition: stored at −80° C.
 Product identification: Anti-CTLA4
 Physical description: 8.71 mg/ml
 Package and storage condition: stored at 4° C.
Experimental Methods and Procedures
Cell Culture The CT-26 cells were maintained in medium supplemented with 10% heat inactivated fetal bovine serum at 37° C. in an atmosphere of 5% $CO_2$ in air. The tumor cells were routinely subcultured twice weekly. The cells growing in an exponential growth phase were harvested and counted for tumor inoculation.

Tumor Inoculation

Each mouse was inoculated subcutaneously at the right flank with CT-26 tumor cells ($3.0 \times 10^5$) in 0.1 mL of PBS for tumor development. Animals were randomized when the average tumor volume reached 66 mm³. The test article administration and the animal numbers in each group were shown in the experimental design table.

After 4 weeks' treatment and ~4 weeks monitor, mouse in group 3 and 4 was inoculated subcutaneously at the left flank with CT-26 tumor cells ($3.0 \times 10^5$) in 0.1 mL of PBS for immune system re-challenge Each mouse is inoculated subcutaneously at the right flank with a tumor fragment (30 mm³) for tumor development. The treatments is started when the average tumor volume reaches 164 mm³.

| Test article | Conc. (mg/mL) | Formulation |
|---|---|---|
| Vehicle | — | 25 mM Histidine 10% sucrose pH7 |
| anti-CTLA4 | 1 | Dilute 689 ul 8.71 mg/ml anti-CTLA-4 with 5.31 ml PBS |
| BT1718 | 0.84 | Dissolve 22.3 mg BT1718 in 34 ml His-buffer* |

*His-buffer: 25 mM Histidine 10% sucrose pH7

Observations

All the procedures related to animal handling, care and the treatment in the study were performed according to the guidelines approved by the Institutional Animal Care and Use Committee (IACUC), following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss, eye/hair matting and any other abnormal effect as stated in the protocol. Death and observed clinical signs were recorded on the basis of the numbers of animals within each subset.

Tumor Measurements and the Endpoints

The major endpoint was to see if the tumor growth could be delayed or mice could be cured. Tumor volume was measured three times weekly in two dimensions using a caliper, and the volume was expressed in mm3 using the formula: $V=0.5 \, a \times b^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.

TGI was calculated for each group using the formula: TGI (%)=$[1-(T_i-T_0)/(V_i-V_0)] \times 100$; $T_i$ is the average tumor volume of a treatment group on a given day, $T_0$ is the average tumor volume of the treatment group on the day of treatment start, $V_i$ is the average tumor volume of the vehicle control group on the same day with $T_i$, and $V_0$ is the average tumor volume of the vehicle group on the day of treatment start.

Statistical Analysis

Summary statistics, including mean and the standard error of the mean (SEM), were provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. T-test was used to compare the difference between 2 groups. All data were analyzed using Graph-Pad 5.0. P<0.05 was considered to be statistically significant.

Results

Figure 5:
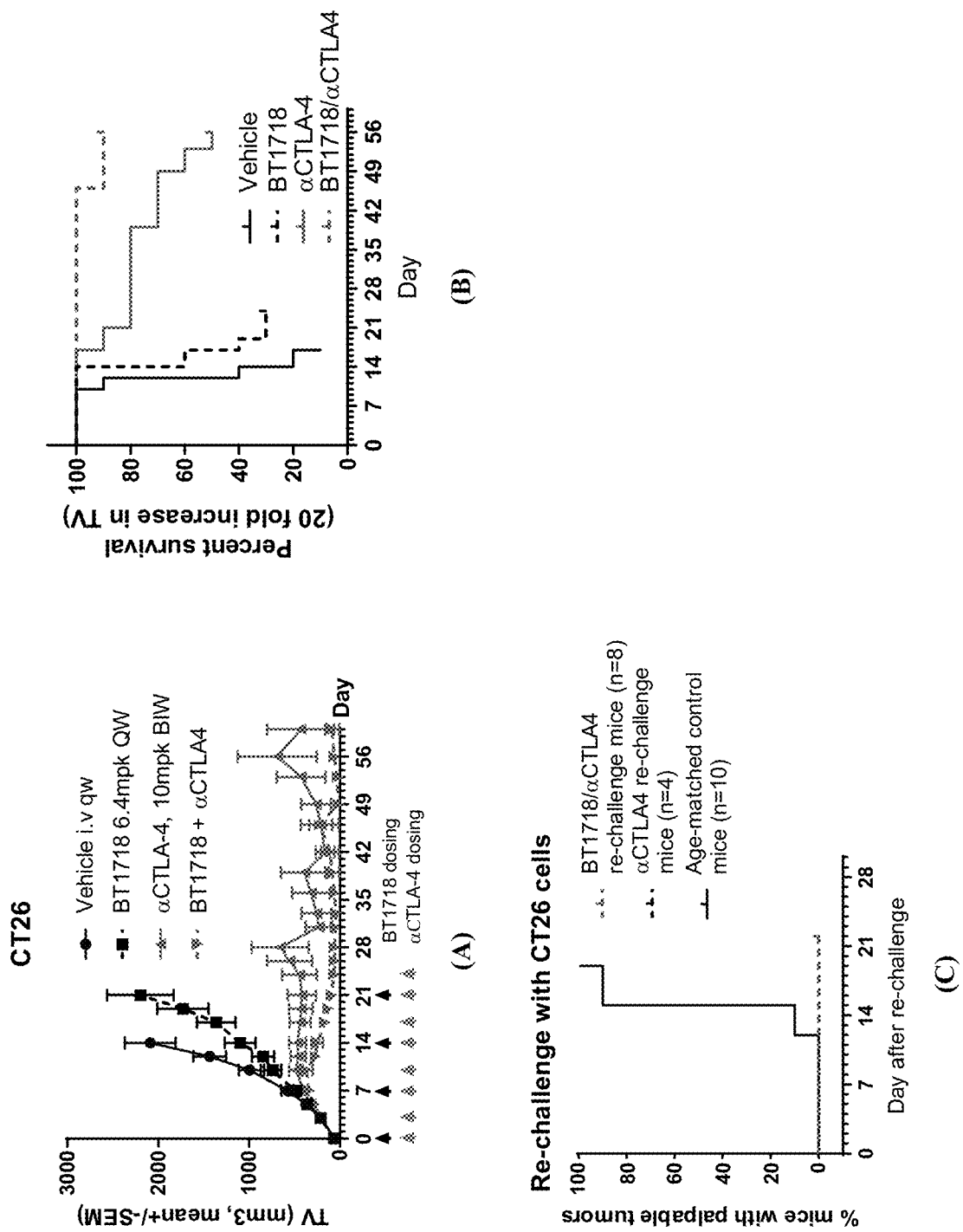
FIG. 5 depicts the tumor volume traces and percentage survival (defined as 20-fold increase in tumor volume) after administering BT1718 and anti-CTLA4 to BALB/c mice bearing CT-26 tumor, and the percentage of tumor re-growth after cell re-inoculation. Data points represent group mean, error bars represent standard error of the mean (SEM). 8/10 mice with CT26 syngeneic tumors are complete responders after BT1718/aCTLA-4 treatment (4/10 after aCTLA-4) and reject the subsequent implantation with CT26-cells.

The tumor volume traces after the treatment are shown in FIG. 5.

Mean tumor volume trace during the treatment period in female BALB/c mice bearing CT26 tumors is shown in Table 4.1.

TABLE 4.1

Tumor volume trace over time

| Days | Group 1 Vehicle, qw | Group 2 811718, 6.4 mpk, qw | Group 3 anti-CTLA4, 10 mpk, biw | Group 4 811718+ anti-CTLA4 |
|---|---|---|---|---|
| 0 | 66 ± 8 | 66 ± 7 | 66 ± 8 | 66 ± 7 |
| 3 | 211 ± 22 | 216 ± 28 | 208 ± 20 | 208 ± 28 |
| 5 | 373 ± 43 | 361 ± 52 | 318 ± 34 | 290 ± 43 |
| 7 | 581 ± 64 | 499 ± 73 | 399 ± 52 | 341 ± 56 |
| 10 | 993 ± 120 | 740 ± 95 | 487 ± 75 | 369 ± 68 |
| 12 | 1433 ± 181 | 848 ± 124 | 461 ± 84 | 269 ± 58 |
| 14 | 2090 ± 281 | 1101 ± 170 | 468 ± 94 | 250 ± 62 |
| 17 | | 1364 ± 212 | 439 ± 117 | 168 ± 48 |
| 19 | | 1730 ± 284 | 430 ± 130 | 132 ± 45 |
| 21 | | 2198 ± 367 | 421 ± 156 | 97 ± 32 |
| 24 | | | 447 ± 190 | 66 ± 24 |
| 26 | | | 554 ± 249 | 61 ± 25 |
| 28 | | | 659 ± 316 | 62 ± 26 |

Tumor Growth Inhibition Analysis

Tumor growth inhibition rate of BT1718 and anti-CTLA4 in the CT-26 syngeneic model was calculated based on tumor volume measurements on day 14 after the start of the treatment.

TABLE 4.2

Tumor growth inhibition analysis

| Group | Treatment | Tumor Volume (mm³)[a] | T/C[b] (%) | TGI (%) | P value (vs vehicle) | P value (vs combo) |
|---|---|---|---|---|---|---|
| 1 | Vehicle, qw | 2090 ± 281 | — | — | — | — |
| 2 | BT1718, 6.4 mpk, qw | 1101 ± 170 | 52.7 | 48.9 | p < 0.001 | p < 0.001 |
| 3 | anti-CTLA4, 10 mpk, biw | 468 ± 94 | 22.4 | 80.1 | p < 0.001 | p < 0.05 |
| 4 | B11718 + anti-CTLA4 | 250 ± 62 | 12.0 | 90.9 | p < 0.001 | — |

Re-Challenge

Mice of group 3 and 4 were kept monitoring after 4 weeks' treatment, and the immune system was re-challenged with CT-26 cells on Day 62. The tumor growth after the cell re-implantation is shown in FIG. 5.

Results Summary and Discussion

In this study, the therapeutic efficacy of BT1718 and Anti-CTLA4 in the CT-26 syngeneic model was evaluated. The measured body weight and tumor volume of all treatment groups at various time points are shown in FIG. 5, and Table 4.1 and 4.2.

The mean tumor volume of vehicle treated mice reached 2090 mm3 on day 14 after the start of treatment. BT1718 at 6.4 mg/kg, qw (TV=1101 mm3, TGI=48.9%, p<0.001) produced obvious anti-tumor activity. Anti-CTLA4 antibody at 10 mg/kg, biw alone (TV=468 mm3, TGI=80.1%, p<0.001) alone or combined with BT1718 (TV=250 mm3, TGI=90.9%, p<0.001) produced potent anti-tumor activity.

The combination of BT1718 and Anti-CTLA4 antibody further improved the anti-tumor effect of BT1718 6.4 mg/kg (p<0.001) or Anti-CTLA4 antibody (p<0.05) 10 mg/kg as single therapy.

4 tumors in group 3 and 8 tumors in group 4 were completely eradicated by the treatments and didn't show any relapse, the immune system in those mice was re-challenged with CT26 cells. As the results, no mice developed tumors after the Anti-CTLA4 Ab alone or in combination with BT1718 treatments in group 3 and 4, whereas 100% mice developed tumors in the control groups.

Animals in all groups maintained the body weights well.

Example 5

BT1718/ANTI-PD-1 Transcriptional Study

Study Objective

The objective of the research is to study the mechanism of the combination effect of BT1718 and Anti-PD-1 in vivo. A set of data was generated to explore the molecular changes in response to BT1718, Anti-PD1 and their combination in syngeneic LLC tumor model. Transcriptional changes were observed indicative of augmented antitumor immunity elicited by combining BT1718 with Anti-PD1. Transcriptional changes indicated Type I IFN response, release of cancer cell antigens, cancer antigen presentation and T cell priming and activation and immune cell infiltration into tumors.

LLC tumor bearing C75Bl/6 mice (n=5) were treated with a single dose of vehicle iv, BT1718 4.8 mg/kg iv, Anti-PD-1 10 mg/kg ip or the combination of BT1718 and Anti-PD-1. Tumors were harvested 24 and 48 h after dosing and RNA was analyzed by Nanostring using the nCounter Mouse PanCancer IO 360 Panel that includes 750 genes covering the key pathways at the interface of the tumor, tumor microenvironment, and immune response. nSolver software was used for data analysis. Despite high variability in the transcriptional profiles of the vehicle treated tumors, enhancement of immune modulation was apparent when BT1718 was combined with PD-1.

Figure 6:
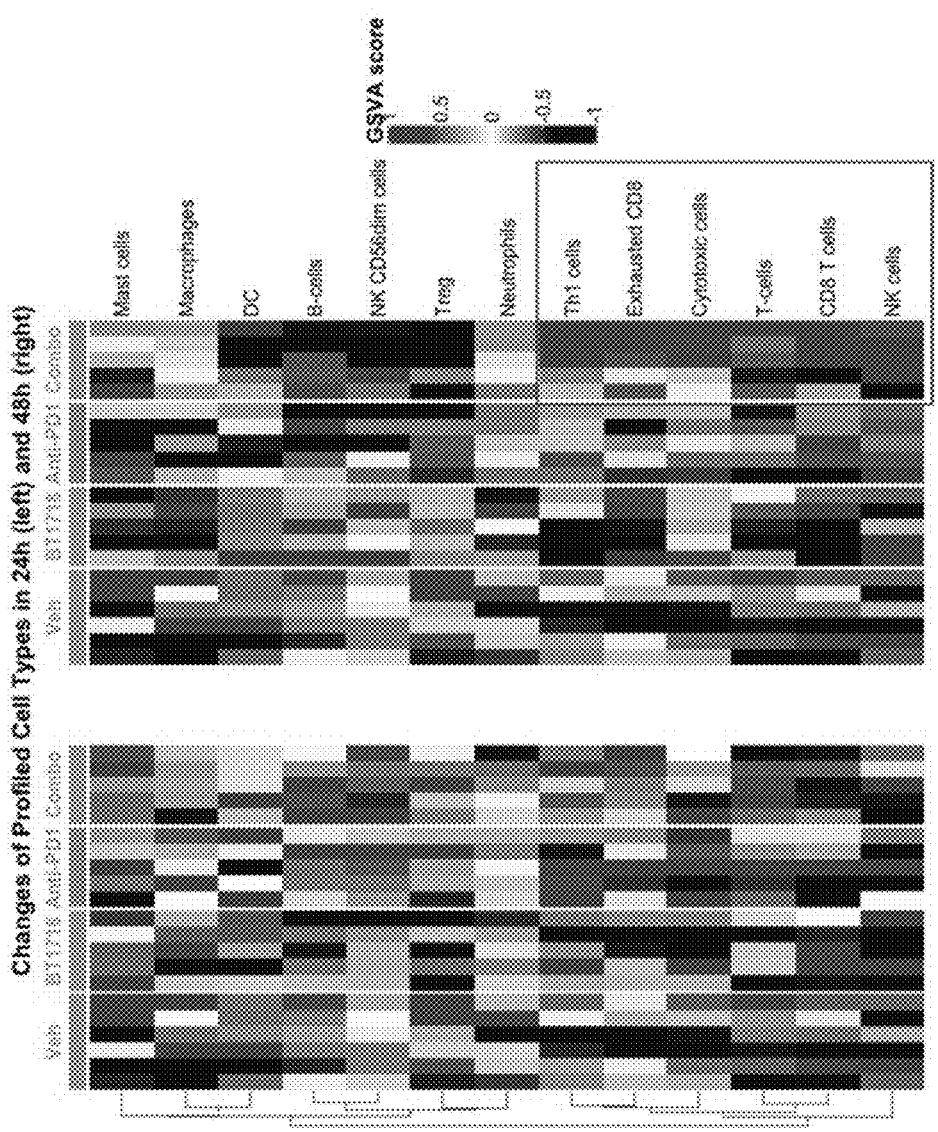
FIG. 6 depicts that functional enrichment analysis indicates an increase in T cell related markers (Th1 cells, Exhausted CD8 cells, Cytotoxic cells, T cells, CD8 T cells) in tumors of animals treated with BT1718/PD-1-combination. These changes become apparent at 48 h timepoint. GSVA score refers to Gene Set Variation Analysis.
Figure 7:
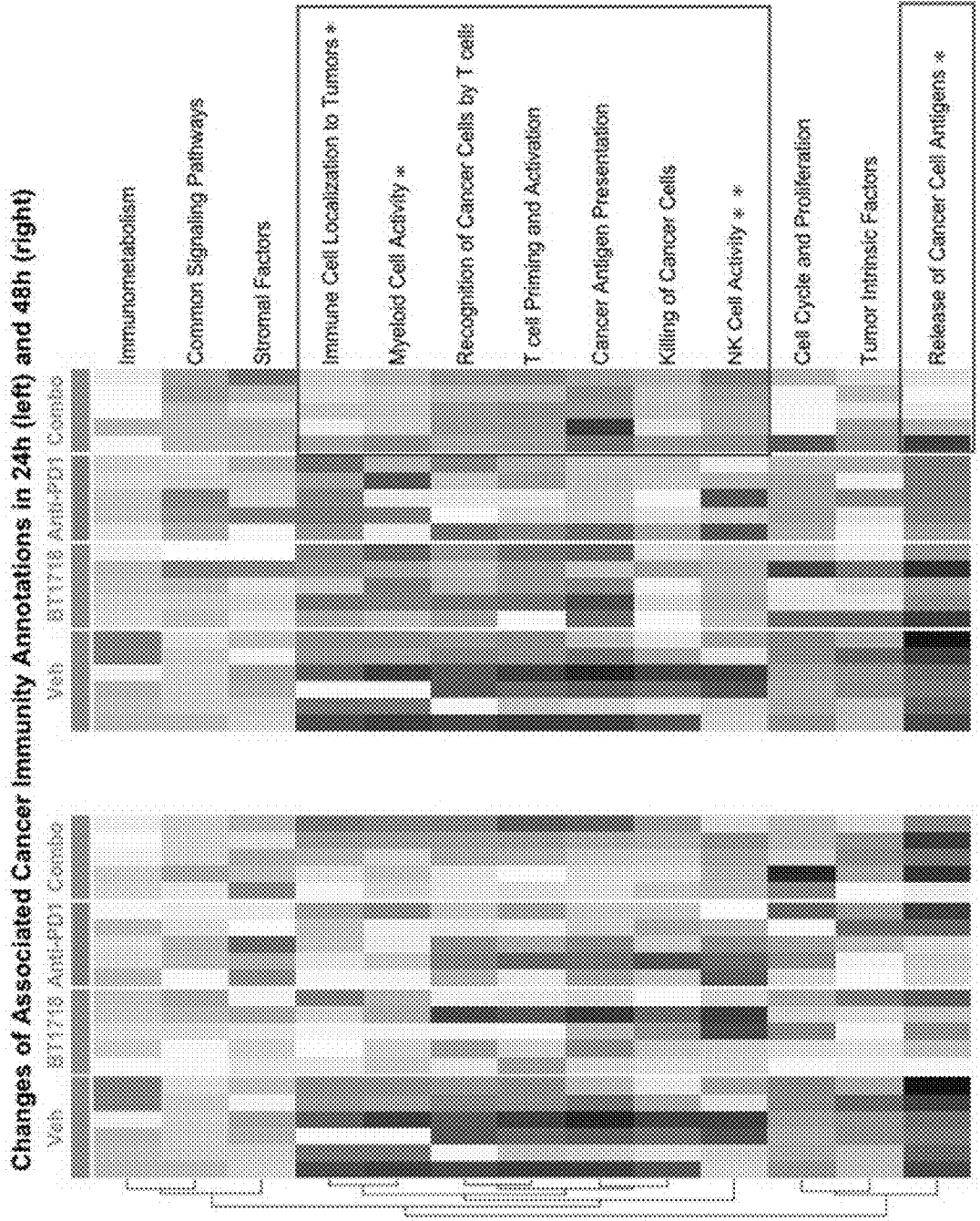
FIG. 7 depicts that, when transcripts are annotated according to anti-cancer immunity functions, the functional enrichment analysis indicates an increase in immune cell localization to tumors, myeloid cell activity, recognition of cancer cells by T cells, T cell priming and activation, cancer antigen presentation and killing of cancer cells in animals treated with BT1718/PD-1-combination. NK cell activity signature is also increased by the combination treatment. Unexpectedly the signature for the release of cancer cell antigen decreases with the combination treatment. These changes become apparent at 48 h timepoint. Color coding refers to the same GSVA score as in FIG. 6. For Immune Cell Localization to Tumors, Myeloid Cell Activity, NK Cell Activity, and Release of Cancer Cell Antigen, adjusted $p<0.1$ (PD1/Combo at 48 h). For NK Cell Activity, adjusted $p<0.05$ (CTR/Combo at 48 h).
Figure 8:
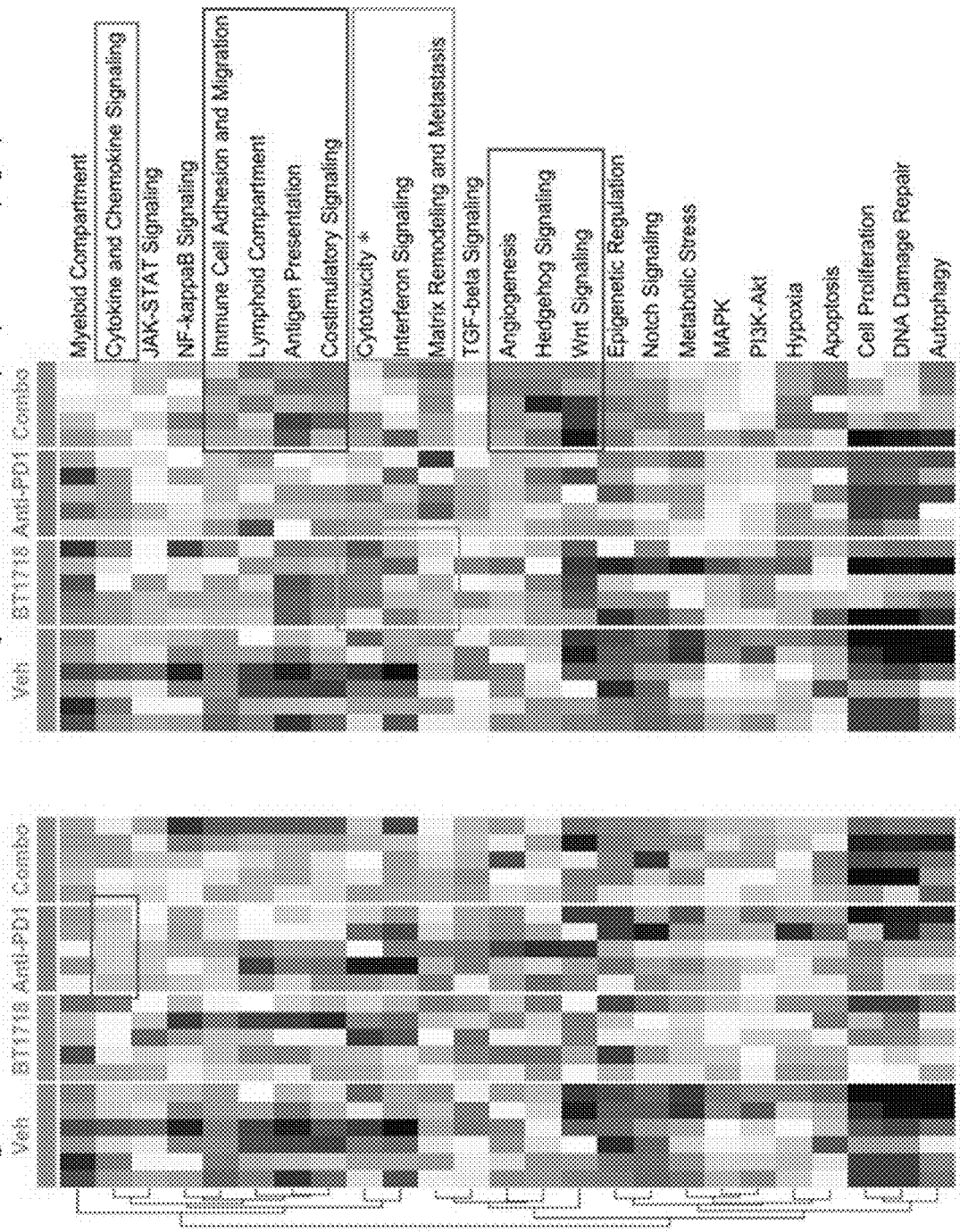
FIG. 8 depicts that functional and pathway annotation of the transcripts indicate modulations in several different tissue functions. The activity of Anti-PD-1 in inducing cytokine and chemokine signaling can be observed at the 24 h timepoint whereas the monotherapy activity of BT1718 becomes apparent at 48 h with increase in signatures for cytotoxicity and IFN signaling and matrix remodeling and metastasis. Transcriptional signature changes in response to the combination treatment can again be observed at the 48 h timepoint. These include increases in immune cell adhesion and migration, lymphoid compartment, antigen presentation and costimulatory signaling. A signal for decrease in hedgehog signaling, angiogenesis and Wnt signaling was indicated by the changes in transcriptional signatures. Color coding refers to the same GSVA score as in FIG. 6. For Cytotoxicity, adjusted $p<0.05$ (CTR/BT1718 at 48 h).

The data and analysis are shown in FIGS. 6-8. Overall the transcriptional analysis of the BT1718 combination effect with Anti-PD1 indicates an increase in immunomodulation at early timepoints brought on by combining the Bicycle toxin conjugate BT1718 with Anti-PD-1 antibody. Based on the data, Nanostring analysis provides a more cost effective way of generating a comprehensive view of the drug effect in tumor tissue (tumor cells, tumor infiltrating immune cells and in the tumor microenvironment in general) that what could be generated by flow cytometry or multiplexed immunofluorescence analysis of tissue sections.

We claim:

1. A method of treating a cancer in a patient, comprising administering to said patient a therapeutically effective amount of BT1718, or a pharmaceutically acceptable salt thereof, and a checkpoint inhibitor, wherein the cancer is a lung cancer or a breast cancer, and wherein the checkpoint inhibitor is an anti-PD1 antibody.

2. The method of claim 1, wherein the cancer is a lung cancer.

3. The method of claim 2, wherein the method comprises administering BT1718, or a pharmaceutically acceptable salt thereof, at a dose of about 9-24 mg/m$^2$.

4. The method of claim 2, wherein the method comprises administering BT1718, or a pharmaceutically acceptable salt thereof, at a dose of about 14-24 mg/m$^2$.

5. The method of claim 2, wherein the method comprises administering BT1718, or a pharmaceutically acceptable salt thereof, at a dose of about 19.2 mg/m$^2$.

6. The method of claim 2, wherein the method comprises administering BT1718, or a pharmaceutically acceptable salt thereof, at a frequency of once a week.

7. The method of claim 1, wherein the cancer is a breast cancer.

8. The method of claim 7, wherein the method comprises administering BT1718, or a pharmaceutically acceptable salt thereof, at a dose of about 19.2 mg/m$^2$.

9. The method of claim 7, wherein the method comprises administering BT1718, or a pharmaceutically acceptable salt thereof, at a frequency of once a week.

10. The method of claim 1, wherein BT1718, or a pharmaceutically acceptable salt thereof, is administered by an intravenous infusion.

11. The method of claim 1, wherein BT1718, or a pharmaceutically acceptable salt thereof, is administered with histidine.

12. The method of claim 1, wherein BT1718, or a pharmaceutically acceptable salt thereof, is administered with sucrose.

13. The method of claim 2, wherein the lung cancer is non-small cell lung cancer.

14. The method of claim 2, wherein the method comprises administering BT1718, or a pharmaceutically acceptable salt thereof, at a dose of about 14.4 mg/m$^2$.

15. The method of claim 2, wherein the method comprises administering BT1718, or a pharmaceutically acceptable salt thereof, at a dose of about 9 mg/m$^2$.

16. The method of claim 7, wherein the method comprises administering BT1718, or a pharmaceutically acceptable salt thereof, at a dose of about 9-24 mg/m$^2$.

17. The method of claim 7, wherein the method comprises administering BT1718, or a pharmaceutically acceptable salt thereof, at a dose of about 14-24 mg/m$^2$.

18. The method of claim 7, wherein the method comprises administering BT1718, or a pharmaceutically acceptable salt thereof, at a dose of about 14.4 mg/m$^2$.

19. The method of claim 1, wherein the method comprises administering BT1718, or a pharmaceutically acceptable salt thereof, at a frequency of once every 2 weeks.

20. The method of claim 1, wherein the anti-PD1 antibody is selected from nivolumab, pembrolizumab, durvalumab, and atezolizumab.

21. The method of claim 1, wherein BT1718, or a pharmaceutically acceptable salt thereof, is administered with the anti-PD1 antibody simultaneously or sequentially in separate unit dosage forms.

* * * * *